United States Patent
Wall et al.

(10) Patent No.: US 10,308,685 B2
(45) Date of Patent: *Jun. 4, 2019

(54) INHIBITORY PEPTIDES OF VIRAL INFECTION

(71) Applicant: UNIVERSITY OF TENNESSEE RESEARCH FOUNDATION, Knoxville, TN (US)

(72) Inventors: Jonathan S. Wall, Knoxville, TN (US); Timothy E. Sparer, Knoxville, TN (US); Stephen J. Kennel, Knoxville, TN (US)

(73) Assignee: UNIVERSITY OF TENNESSEE RESEARCH FOUNDATION, Knoxville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/605,877

(22) Filed: May 25, 2017

(65) Prior Publication Data

US 2017/0267722 A1 Sep. 21, 2017

Related U.S. Application Data

(63) Continuation of application No. 14/801,717, filed on Jul. 16, 2015, now Pat. No. 9,683,017.

(60) Provisional application No. 62/025,912, filed on Jul. 17, 2014.

(51) Int. Cl.

| | |
|---|---|
| A61K 38/36 | (2006.01) |
| A61K 39/395 | (2006.01) |
| A61K 47/66 | (2017.01) |
| A61K 51/10 | (2006.01) |
| C07K 7/08 | (2006.01) |
| C07K 16/18 | (2006.01) |
| C07K 14/00 | (2006.01) |
| A61K 38/16 | (2006.01) |
| C07K 14/035 | (2006.01) |
| C07K 14/045 | (2006.01) |

(52) U.S. Cl.
CPC ............ C07K 7/08 (2013.01); A61K 38/16 (2013.01); C07K 14/001 (2013.01); C07K 14/035 (2013.01); C07K 14/045 (2013.01)

(58) Field of Classification Search
CPC ............. A61K 38/16; A61K 2039/505; A61K 2039/545; A61K 38/1716; A61K 39/395; A61K 39/39583; A61K 47/66; A61K 47/6891; A61K 51/10; C07K 14/001; C07K 14/035; C07K 14/045; C07K 7/08; C07K 14/4711; C07K 16/18; C07K 2317/34; C07K 2319/00; C07K 2319/70
USPC ......... 514/3.8, 4.2; 530/324, 326; 435/235.1
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 4,902,505 A | 2/1990 | Pardridge et al. | |
| 4,957,735 A | 9/1990 | Huang | |
| 5,004,697 A | 4/1991 | Pardridge | |
| 5,019,369 A | 5/1991 | Presant et al. | |
| 5,055,303 A | 10/1991 | Riley, Jr. | |
| 5,091,309 A | 2/1992 | Schlesinger et al. | |
| 5,188,837 A | 2/1993 | Domb | |
| 5,217,879 A | 6/1993 | Huang et al. | |
| 5,254,342 A | 10/1993 | Shen et al. | |
| 5,268,164 A | 12/1993 | Kozarich et al. | |
| 5,271,961 A | 12/1993 | Mathiowitz et al. | |
| 5,413,797 A | 5/1995 | Khan et al. | |
| 5,506,206 A | 4/1996 | Kozarich et al. | |
| 5,514,670 A | 5/1996 | Friedman et al. | |
| 5,534,496 A | 7/1996 | Lee et al. | |
| 5,561,107 A * | 10/1996 | Jaynes ................. | A61K 38/10 435/375 |
| 6,153,596 A * | 11/2000 | Liotta .................... | A61K 48/00 435/6.14 |
| 7,476,786 B2 * | 1/2009 | Chan ..................... | B82Y 30/00 435/6.14 |
| 8,791,243 B2 | 7/2014 | Schenk et al. | |
| 2002/0019335 A1 | 2/2002 | Soloman et al. | |
| 2002/0031527 A1 | 3/2002 | Wu et al. | |
| 2002/0115717 A1 | 8/2002 | Gervais et al. | |

(Continued)

FOREIGN PATENT DOCUMENTS

| | | |
|---|---|---|
| WO | 1999060024 | 11/1999 |
| WO | 2010011999 | 1/2010 |

(Continued)

OTHER PUBLICATIONS

Borst et al., "A peptide inhibitor of cytomegalovirus infection from human hemofiltrate", Antimicrob Agents Chemother. Oct. 2013;57(10):4751-60. doi: 10.1128/AAC.00854-13. Epub Jul. 15, 2013.

(Continued)

*Primary Examiner* — Julie Ha
(74) *Attorney, Agent, or Firm* — Fisherbroyles, LLP; Jason M. Pass

(57) ABSTRACT

Disclosed are methods of treating and/or inhibiting a viral infection in a subject. The methods include administering a therapeutically effective amount of heparin-binding peptide. Also disclosed herein are methods for blocking viral binding to a cell. Further disclosed are anti-viral compositions for administration to a subject infected with a virus. Administration of the anti-viral composition inhibits viral infection of the subject.

16 Claims, 9 Drawing Sheets

Specification includes a Sequence Listing.

(56) References Cited

U.S. PATENT DOCUMENTS

| | | |
|---|---|---|
| 2004/0146512 A1 | 7/2004 | Rosenthal |
| 2009/0017017 A1 | 1/2009 | Rasmussen et al. |
| 2009/0232733 A1 | 9/2009 | O'Nuallain et al. |
| 2010/0003259 A1 | 1/2010 | Ruben et al. |
| 2012/0321555 A1 | 12/2012 | Schenk |
| 2013/0022546 A1 | 1/2013 | Wall et al. |
| 2013/0210168 A1 | 8/2013 | Mead |
| 2015/0158937 A1 | 6/2015 | Schenk et al. |
| 2016/0243230 A1* | 8/2016 | Wall .............. C07K 14/4711 |

FOREIGN PATENT DOCUMENTS

| | | |
|---|---|---|
| WO | 2011119608 | 9/2011 |
| WO | 2012037498 | 3/2012 |

OTHER PUBLICATIONS

Jaishankar et al., "Characterization of a proteolytically stable D-peptide that suppresses herpes simplex virus 1 infection: implications for the development of entry-based antiviral therapy", J Virol. Feb. 2015;89(3):1932-8. doi: 10.1128/JVI.02979-14. Epub Nov. 26, 2014.

Ostrander, et al., Anti-viral activity of human recombinant heparin-binding proteins HBNF and MK, Biochem Biophys Res Commun. Dec. 15, 1992;189(2):1189-95.

Schmidtke et al.,"Binding of a N,N'-bisheteryl derivative of dispirotripiperazine to heparan sulfate residues on the cell surface specifically prevents infection of viruses from different families", Virology. Jun. 20, 2003;311(1):134-43.

Tiwari et al., "Anti-heparan sulfate peptides that block herpes simplex virus infection in vivo", J Biol Chem. Jul. 15, 2011;286(28):25406-15. doi: 10.1074/jbc.M110.201103. Epub May 19, 2011.

O'Nuallain et al., Phage display and peptide mapping of an immunoglobulin light chain fibril-related conformational epitope, Biochemistry. Nov. 13, 2007;46(45):13049-58. Epub Oct. 18, 2007.

O'Nuallain et al., "Localization of a conformational epitope common to non-native and fibrillar immunoglobulin light chains", Biochemistry. Feb. 6, 2007;46(5):1240-7.

Wall et al., "Preclinical Validation of the Heparin-Reactive Peptide p5+14 as a Molecular Imaging Agent for Visceral Amyloidosis", Molecules. Apr. 27, 2015;20(5):7657-82. doi: 10.3390/molecules20057657.

Wall et al., "Generation and Characterization of anti-AA Amyloid-Specific Monoclonal Antibodies", Frontiers of Immunology, 2011, doi:10.3389/fimmu.2011.00032.

International Search Report and Written Opinion issued in PCT/US2015/046523 dated Jan. 28, 2016 (16 pages).

Invitation to Pay Additional Fees issued in PCT/US2015/046523 dated Nov. 8, 2015 (3 pages).

Image File Wrapper of International Patent Application No. PCT/US2015/046523 filed Aug. 24, 2015, Applicant University of Tennessee Research Foundation.

International Search Report and Written Opinion issued in PCT/US17/15905 dated Jun. 9, 2017, Applicant University of Tennessee Research Foundation (19 pages).

International Search Report and Written Opinion issued in PCT/US17/28828 dated Sep. 13, 2017, Applicant University of Tennessee Research Foundation (21 pages).

Image File Wrapper of U.S. Appl. No. 14/801,717, filed Jul. 16, 2015, first named inventor Jonathan S. Wall.

Image File Wrapper of U.S. Appl. No. 15/052,772, filed Feb. 24, 2016, first named inventor Jonathan S. Wall.

Baden et al., "Light Chain Amyloidosis—Current Findings and Future Prospects", Current Protein and Peptide Science, 2009, 10:500-508.

Image File Wrapper of International Patent Application No. PCT/US2017/015905 filed Jan. 31, 2017, Applicant University of Tennessee Research Foundation.

Supplementary European Search Report issued in EP 15836458.8 dated Apr. 5, 2018 (10 pages).

Funke et al., "Peptides for Therapy and Diagnosis of Alzheimer's Disease", Current Pharmaceutical Design, 18(6):755-767, 2012.

Goure et al., "Targeting the proper amyloid-beta neuronal toxins: a path forward for Alzheimer's disease immunotherapeutics", Alzheimers Res Ther, 6(4):42, 2014.

Lobello et al., "Targeting Beta Amyloid: A Clinical Review of Immunotherapeutic Approaches in Alzheimer's Disease", International Journal of Alzheimer's Disease, 6(4):S305-14, 2012.

Wall et al., "Development and evaluation of agents for targeting visceral amyloid", Journal of Drug Targeting, 33(4):807-814, 2011.

Wall et al., "Pretargeting immunotherapy: a novel treatment approach for systemic amyloidosis", Pharmaceutical Patent Analyst, 6(5):215-223, 2017.

Wall et al., "A bifunctional peptide, "peptope", for pre-targeting antibody 7D8 to systemic amyloid deposits", Amyloid, 24(16):22-23, 2017.

* cited by examiner

INHIBITORY PEPTIDES OF VIRAL INFECTION

CROSS-REFERENCE TO RELATED APPLICATIONS

This application is a continuation of U.S. patent application Ser. No. 14/801,717, filed Jul. 16, 2015, titled "Inhibitory Peptides of Viral Infection", which claims priority to U.S. Provisional Application No. 62/025,912, filed Jul. 17, 2014, titled "Inhibitory Peptides of Viral Infection." The entire disclosure of each of the above-identified applications is hereby fully incorporated herein by reference.

STATEMENT OF GOVERNMENT SUPPORT

This invention was made with government support under grant number R01 DK079984 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 25, 2017, is named 05820_003US2_SeqListing.txt and is 11 kilobytes in size.

The nucleic acid and/or amino acid sequences listed herein are shown using standard letter abbreviations for nucleotide bases, and three letter code or one letter codes for amino acids, as defined in 37 C.F.R. § 1.822. Only one strand of the nucleic acid sequence is shown, but the complementary strand is understood as included by any reference to the displayed strand.

FIELD OF THE INVENTION

The present disclosure is directed, generally, to the inhibition of viral infection, and to the treatment of diseases associated with viral infections. More specifically, the present disclosure provides heparin-binding peptides that can block and inhibit viral infection.

BACKGROUND

Viruses, unlike bacteria, rely on the host cell for their replication. The first step of a virus's lifecycle is attachment to the host cell. This attachment to initiate replication often relies on the interaction of viral proteins attaching to poly saccharides found in the extracellular matrix (ECM) surrounding the cells. One of the linear polysaccharides in the ECM that viruses use is heparan sulfate (HS). A variety of different virus families use heparan sulfate for entry including members of the Herpesviridae, Paramyxoviridae, Picornaviridae, Parvoviridae, Retroviridae, and Poxviridae. Although the exact mechanism of attachment is unknown, it is assumed that blocking entry into the host cell will prevent virus infection and limit viral spread within the host.

Heparan sulfate (HS) when present on a cell surface, provides an attachment site for many human and non-human pathogenic viruses including herpes simplex virus type-1 and -2 (HSV-1 and HSV-2, respectively). HSV binds to heparan sulfate and HSV-1 penetration into cells can also be mediated by 3-OS heparan sulfate, which is produced after a rare enzymatic modification in HS catalyzed by 3-O-sulfortransferases (3-OSTs). HSV envelope glycoproteins B and C (gB and gC) bind HS and mediate virus attachment to cells. A third glycoprotein, gD, specifically recognizes 3-OS HS in a binding interaction that facilitates fusion pore formation during viral entry.

The versatility of HS to bind multiple microbes and participate in a variety of regulatory phenomena comes from its negatively-charged nature and highly complex structure, which is generated by enzymatic modifications. Virtually all cells express HS as long un-branched chains often associated with protein cores commonly exemplified by syndecan, perlecan and glypican families of HS proteoglycans. The parent HS chain, which contains repeating glucosamine and hexuronic acid dimers, can be 100-150 residues long and may contain multiple structural modifications. Most common among them is the addition of sulfate groups at various positions within the chain, which leads to the generation of specific "heparin-like" highly electronegatively charged motifs making HS very attractive for viral and microbial adherence.

Emerging evidence suggests that the role of HS in viral infection extends beyond its function as a low-specificity pre-attachment site. For instance, HS mediates HSV-1 transport on filopodia during surfing (and negatively regulates virus-induced membrane fusion). Likewise, for human papilloma virus (HPV), HS proteoglycans play a key role in the activation of immune response, an important aspect for both vaccine development and HPV pathogenesis. Similarly, HS expressed on spermatozoa plays a key role in the capture of human immunodeficiency virus (HIV) and its transmission to dendritic, macrophage, and T-cells. Further, the first step during cytomegalovirus CMV infection is attachment via HS, and then subsequent steps follow. Heparan sulfate also plays a role in hepatitis B virus replication.

Despite the promise shown by HS in the development of a viral therapy, what remains critically needed are anti-HS inhibitors that prevent the cellular infection by viruses, including HSV and CMV. For example, therapeutics that target HS—and thus a critical step in HSV and CMV infection of the host cell—would be valuable, inasmuch as current therapeutics for these and other viral infections include antiviral drugs. But problems with the current antiviral drugs include increased viral resistance and harmful side effects, like nephrotoxicity. New therapeutics are thus needed that are both less toxic and are less likely to trigger resistance in infections such as HSV and CMV infections.

SUMMARY

In certain example aspects described herein, a method for inhibiting viral infection is provided. For example, a subject in whom a viral infection is to be inhibited is selected. The subject is then administered an effective amount of heparin-binding peptide of specified sequence as described herein. Administration of the heparin-binding peptide thereby inhibits the viral infection in the subject. The viral infection, for example, may be a herpesvirus, cytomegalovirus, human immunodeficiency virus infection, or other viruses as described herein. The heparin-binding peptide may be an L-form peptide or, in other aspects, a D-form peptide as described herein.

In certain other example aspects described herein, a method for blocking binding of a virus to a cell is provided. For example, a cell is contacted with an effective amount of a heparin-binding peptide, the heparin-binding peptide comprising an amino acid sequence as described herein.

In certain other aspects described herein, an anti-viral composition is provided. For example, the composition includes a heparin-binding peptide comprising one or more amino acid sequences as described herein. The heparin-binding peptide may be present in the composition in an effective amount, for example, to inhibit viral infection in a subject infected with a virus by at least 60%.

These and other aspects, objects, features and advantages of the example embodiments will become apparent to those having ordinary skill in the art upon consideration of the following detailed description of illustrated example embodiments.

DETAILED DESCRIPTION OF THE EXAMPLE EMBODIMENTS

I. Summary of Terms

Figure 1:
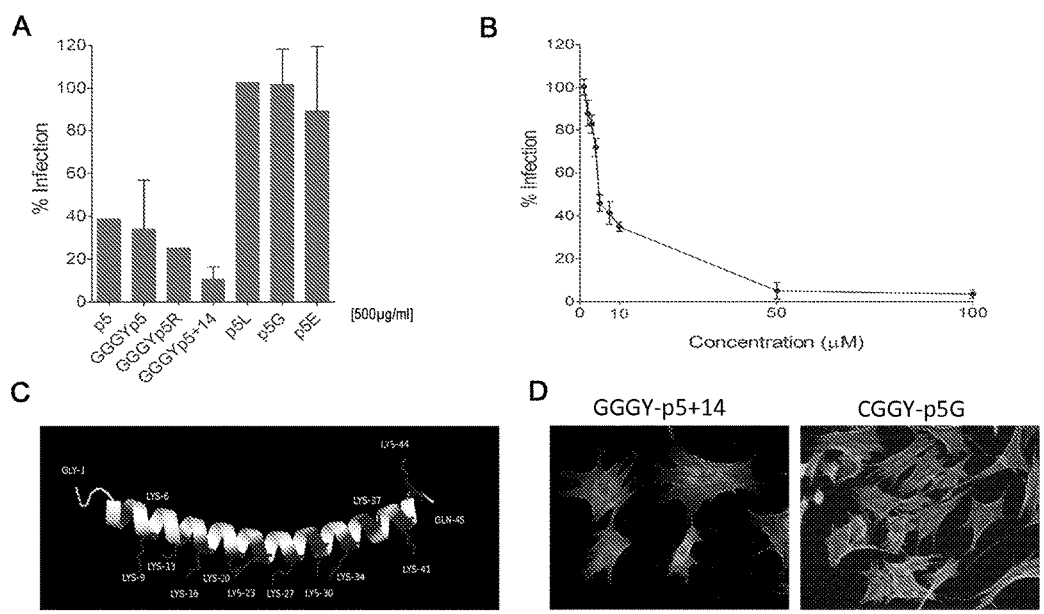
FIG. 1. Heparin-reactive peptides reduce MCMV infection in vitro. (A) Basic synthetic peptides selectively reduced murine cytomegalovirus (MCMV) plaque formation using the plaque reduction assay (n=3). (B) The peptide GGGY-p5+14 (SEQ ID NO: 25) is effective over a range of concentrations. (C) Predicted structure of the peptide GGGY-p5+14 (SEQ ID NO: 25) aligns basic side chains along one face of an α-helix. (D) Biotinylated peptide GGGY-p5+14 (SEQ ID NO: 25) bound MEF 10.1 cells (red fluorescence, left panel) but not the control peptide biotinylated-p5G (right).

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references. As used herein, the singular forms "a," "an," and "the," refer to both the singular as well as plural, unless the context clearly indicates otherwise. The abbreviation, "e.g." is derived from the Latin exempli gratia, and is used herein to indicate a non-limiting example. Thus, the abbreviation "e.g." is synonymous with the term "for example." As used herein, the term "comprises" means "includes."

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject. In some examples a chemotherapeutic is administered to a subject. In some examples, disclosed peptides are administered to a subject.

Animal: Living multi-cellular vertebrate organisms, a category that includes, for example, mammals and birds. The term mammal includes both human and non-human mammals. Similarly, the term "subject" includes both human and veterinary subjects. In some examples a subject is a subject, such as a subject suffering from a viral infection, such as a herpes virus infection.

Effective amount or Therapeutically effective amount: The amount of agent, such as a an antiviral agent, that is sufficient to prevent, treat (including prophylaxis), reduce and/or ameliorate the symptoms and/or underlying causes of any of a disorder or disease, for example to prevent, inhibit, and/or treat a viral infection. In some embodiments, an "effective amount" is sufficient to reduce or eliminate a symptom of a disease, such as a viral infection.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et ah, Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Inhibit: To reduce by a measurable degree.

Inhibiting or treating a disease: Inhibiting the full development of a disease or condition, for example, for example a viral infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component, such as a peptide (for example one or more of the peptides disclosed herein), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors, such as adenoviral vectors, comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well. A first sequence is an "antisense" with respect to a second sequence if a polynucleotide whose sequence is the first sequence specifically hybridizes with a polynucleotide whose sequence is the second sequence.

Pharmaceutically acceptable carriers: The pharmaceutically acceptable carriers of use are conventional. *Remington's Pharmaceutical Sciences*, by E. W. Martin, Mack Publishing Co., Easton, Pa., 19$^{th}$ Edition (1995), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. In some examples, a peptide is one or more of the peptides disclosed herein.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. *Nuc. Acids Res.* 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell. An "anti-viral agent" is an agent that specifically inhibits a virus from replicating or infecting cells.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. The term vector includes plasmids, linear nucleic acid molecules, and as described throughout adenovirus vectors and adenoviruses.

Virus: Microscopic infectious organism that reproduces inside living cells. A virus consists essentially of a core of nucleic acid surrounded by a protein coat, and has the ability to replicate only inside a living cell, for example as a viral infection. "Viral replication" is the production of additional virus by the occurrence of at least one viral life cycle. A virus, for example during a viral infection, may subvert the host cells' normal functions, causing the cell to behave in a manner determined by the virus. For example, a viral infection may result in a cell producing a cytokine, or responding to a cytokine, when the uninfected cell does not normally do so. Many viruses (e.g. influenza and many animal viruses) have viral envelopes covering their protein capsids. The envelopes typically are derived from portions of the host cell membranes (phospholipids and proteins), but include some viral glycoproteins. Functionally, viral envelopes are used to help viruses enter host cells. Glycoproteins on the surface of the envelope serve to identify and bind to receptor sites on the host's membrane. The viral envelope then fuses with the host's membrane, allowing the capsid and viral genome to enter and infect the host.

Examples of Enveloped Viruses in include: DNA viruses, such as Herpesviruses, Poxviruses, Hepadnaviruses: RNA viruses, such as Flavivirus, Togavirus, Coronavirus, Hepatitis D, Orthomyxovirus, Paramyxovirus, Rhabdovirus, Bunyavirus, Filovirus and Retroviruses. In some examples a virus is a human pathogen, such as influenza, RSV, HIV, Rotavirus, New Castle Disease Virus, Marek Disease Virus, Metapneumovirus, Parainfluenza viruses, Coronaviruses (including for example, SARS-CoV, HcoV-HKU1, HcoV-NL63 and TGEV), Hepatitis C virus, Flaviviruses (such as Dengue virus, Japanese Encephlitis virus, Kunjin virus, Yellow fever virus and West Nile virus), Filoviruses (such as Ebola virus and Marburg Virus), Caliciviruses (including Norovirus and Sapovirus), Human Papilloma Virus, Epstein Barr Virus, Cytomegalovirus, Varicella Zoster virus, and Herpes Simplex Virus amon, Birnaviridae, Chrysoviridae, Cystoviridae, Hypoviridae, Partitiviridae, Reoviridae (such as Rotavirus), Totiviridae, Nidovirales, Arteriviridae, Coronaviridae (such as Coronavirus and SARS), Roniviridae, Astroviridae, Barnaviridae, Bromoviridae, Caliciviridae, Closteroviridae, Comoviridae, Dicistroviridae, Flaviviridae (such as Yellow fever virus, West Nile virus, Hepatitis C virus, and Dengue fever virus), Flexiviridae, Hepeviridae (such as Hepatitis E virus), Leviviridae, Luteoviridae, Marnaviridae, Narnaviridae, Nodaviridae Picornaviridae (such as Poliovirus, the common cold virus, and Hepatitis A virus), Potyviridae, Sequiviridae, Tetraviridae, Togaviridae (such as Rubella virus and Ross River virus), Tombusviridae, and Tymoviridael, Bornaviridae (such as Borna disease virus), Filoviridae (such as Ebola virus and Marburg virus, Paramyxoviridae (such as Measles virus, and Mumps virus), Rhabdoviridae (such as Rabies virus), Arenaviridae (such as Lassa fever virus), Bunyaviridae (such as Hantavirus), and Orthomyxoviridae (such as Influenza viruses) among others.

II. Description of Several Embodiments

A. Introduction

Human cytomegalovirus (HCMV) is a beta-herpesvirus with nearly 90% prevalence in the adult human population in developing countries (1). Virus infection is generally asymptomatic in immune competent individuals. However, severe CMV disease occurs in individuals with a deficient immune system e.g., transplant patients suppressed to avoid graft rejection, late stage AIDS patients, and congenitally infected infants. In immune deficient adults reactivated HCMV-disease can cause pneumonitis, multi-organ disease, and death (2-4). Retinitis and blindness are also common in HCMV-infected, late-stage AIDS patients in the absence of highly active antiretroviral therapies (2, 4). In utero infection can cause neurological sequelae in infants, including sensorineuronal hearing loss (SNHL) and mental retardation (1, 3).

Attempts to develop a vaccine for CMV infection are ongoing but have met with limited success (5, 6). Current regimens to treat HCMV infection (e.g., ganciclovir, foscarnet, and cidofovir) target viral DNA synthesis (7) but are nephrotoxic (8). Furthermore the increasing use of these drugs has led to HCMV developing resistance to these therapies (9-12). Due to the limitations of current treatment modalities, it is clinically important to develop new therapeutics against HCMV that are selective, less toxic, and circumvent resistance, i.e., preferably target other aspects of the HCMV life cycle.

Virtually all cells express heparan sulfate (HS) glycosaminoglycans as long un-branched chains associated with protein cores in the form of cell-surface heparan sulfate proteoglycans (HSPGs) (13). Heparan sulfate and heparin are both linear glycosaminoglycans (GAGs) composed of alternating glucosamine and uronic acids that may be N-acetylated and N-sulfated (14-16). Heparan sulfate generally differs from heparin because the latter has a very high frequency of N-sulfation (>80%) on the glucosamine and high O-sulfation (15, 16). Therefore, in basic terms, heparin is considered more electronegative than heparan sulfate GAGs.

HSPGs act as a docking site for growth factors (15-17), parasites such as the malarial sporozoite (18), pathologic amyloid-related proteins (19), and many human and non-human pathogenic viruses including human cytomegalovirus (HCMV) (20) and herpes simplex virus (HSV) (21). The HCMV envelope glycoproteins gB and the gM/gN heterodimer complex bind to heparin and are involved in virus adsorption via interaction with HSPG expressed on the cell surface (20). The ability of HS to act as a binding site for numerous distinct viruses can be attributed to its diverse structure and variable negative charge density (13, 22, 23). Despite the critical role that HS has in HCMV infection, therapeutics targeting HS to treat CMV infections are lacking, likely due to its ubiquitous expression on mammalian cells and its important role in facilitating the biological activity of growth factors.

Recently, a panel of heparin-reactive peptides has been shown to preferentially bind the HSPG GAGs associated with pathologic deposits containing amyloid fibrils, in vitro and in vivo using mouse model of reactive (AA) amyloidosis (24). Of these peptides, a synthetic, 31 amino-acid, polybasic peptide with a +8 net positive charge, designated p5, was shown by single photon emission tomographic (SPECT) imaging and micro-autoradiography to bind AA amyloid in visceral organs, including the liver, spleen, heart, and kidneys (25). Notably, this peptide was does not bind to HS-related GAGs expressed in healthy (i.e., amyloid-free) organs and tissues. Specific reactivity with amyloid-associated HSPG and not healthy tissues likely resulted from its binding to hypersulfated heparan sulfate that is electrochemically similar to heparin (26, 27).

As disclosed herein a panel of synthetic, heparin-reactive, p5-related peptides was tested to identify novel inhibitors of CMV-HS mediated adsorption and subsequent infection. The mechanism of action of the peptide was explored to discern whether the peptide mediated its effects by binding to the virus or the susceptible cells.

Current vaccines do not provide complete protection from CMV infection and anti-CMV drugs, which target viral DNA replication, are associated with toxic side effects. With the increased use anti-virals, drug resistant strains of CMV are becoming prevalent. Therefore, therapies targeting alternate steps of the virus lifecycle need to be developed. As disclosed herein synthetic peptides have been developed that inhibit CMV and herpes simplex virus entry into the cells. In one example, the peptide p5+14 does not neutralize the virus itself but instead binds to the cell surface heparan sulfate to mediate its affect. Given this mode of action, p5+14 can be used to treat drug resistant strains of CMV with a low probability that the virus could develop resistance to this treatment.

B. Methods of Treatment and Inhibition of Viral Disease

This disclosure relates to methods for inhibiting a viral infection in a subject. These methods include, for example, selecting a subject in whom the viral infection is to be inhibited and administering an effective amount of the disclosed HS/heparin-binding polypeptides or nucleic acids encoding such polypeptides. In some embodiments, the methods can include selecting a subject in need of treatment. In some embodiments, a subject who already has a viral infection is selected for administration of an effective amount of the disclosed polypeptides or nucleic acids encoding such polypeptides. In other embodiments, a subject who does not yet have a viral infection is selected for administration of an effective amount of the disclosed polypeptides or nucleic acids encoding such polypeptides. For example, the subject has been exposed to a virus that may result in a viral infection in the subject.

In some embodiments the viral infection is an infection with an enveloped virus, such as an enveloped DNA virus or an enveloped RNA virus. In some examples a virus is a human pathogen, such as influenza, RSV, HIV, Rotavirus, New Castle Disease Virus, Marek Disease Virus, Metapneumovirus, Parainfluenza viruses, Coronaviruses (including for example, SARS-CoV, HcoV-HKU1, HcoV-NL63 and TGEV), Hepatitis C virus, Flaviviruses (such as Dengue virus, Japanese Encephlitis virus, Kunjin virus, Yellow fever virus and West Nile virus), Filoviruses (such as Ebola virus and Marburg Virus), Caliciviruses (including Norovirus and Sapovirus), Human Papilloma Virus, Epstein Barr Virus, Cytomegalovirus, Varicella Zoster virus, and Herpes Simplex Virus amon, Birnaviridae, Chrysoviridae, Cystoviridae, Hypoviridae, Partitiviridae, Reoviridae (such as Rotavirus), Totiviridae, Nidovirales, Arteriviridae, Coronaviridae (such as Coronavirus and SARS), Roniviridae, Astroviridae, Barnaviridae, Bromoviridae, Caliciviridae, Closteroviridae, Comoviridae, Dicistroviridae, Flaviviridae (such as Yellow fever virus, West Nile virus, Hepatitis C virus, and Dengue fever virus), Flexiviridae, Hepeviridae (such as Hepatitis E virus), Leviviridae, Luteoviridae, Marnaviridae, Narnaviridae, Nodaviridae Picornaviridae (such as Poliovirus, the common cold virus, and Hepatitis A virus), Potyviridae, Sequiviridae, Tetraviridae, Togaviridae (such as Rubella virus and Ross River virus), Tombusviridae, and Tymoviridael, Bornaviridae (such as Borna disease virus), Filoviridae (such as Ebola virus and Marburg virus, Paramyxoviridae (such as Measles virus, and Mumps virus), Rhabdoviridae (such as Rabies virus), Arenaviridae (such as Lassa fever virus), Bunyaviridae (such as Hantavirus), and Orthomyxoviridae (such as Influenza viruses) among others.

In some embodiments, heparin-binding peptides for use in the disclosed methods included at least about 15% positively charged amino acids such as arginine and/or lysine. The peptides comprise from about 15% to about 50%, about 20% to about 45%, about 25% to about 40%, or about 30% to about 35% positively charged amino acids. In one embodiment, the heparin-binding peptides include the amino acid sequence XBXXBXXXBXXBXXXBXXBXXXBXXBX (SEQ ID NO: 1), wherein X is any amino acid including a modified amino acid that is not charged; and, B is a positively charged amino acid. In some embodiments, the heparin-binding include SEQ ID NO: 1, wherein X is alanine, glutamine, valine, serine, threonine, or glycine and B is arginine, lysine, or histidine. In some embodiments, the heparin-binding peptide includes the amino acid sequence BXZBXZXBZXBZXZBXZBXZXBZXBZ (SEQ ID NO: 2), wherein, B is arginine, lysine, or histidine; X is isoleucine, leucine, methionine, valine, glycine, phenylalanine, tryptophan, tyrosine, serine, threonine, asparagine, glutamine or a modified amino acid that is not charged; and Z is isoleucine, leucine, methionine, valine, glycine, phenylalanine, tryptophan, tyrosine, serine, threonine, asparagine, or a modified amino acid that is not charged. In certain embodiments, the heparin-binding peptide includes the amino acid sequence RAQRAQARQARQAQRAQRAQARQARQ (SEQ ID NO: 15). In certain embodiments, the heparin-binding peptide includes the amino acid sequence KAQKAQAKQAKQAQKAQKAQAKQAKQ (SEQ NO: 16). In other embodiments, the heparin binding peptides have between about 1 and about 10, such as 1, 2, 3, 4, 5, 6, 7, 8, 9, 10, or even greater repeats of the sequence, KAQKAQA (SEQ ID NO: 17) and or KQAKQAQ (SEQ ID NO: 18). In some examples, the heparin-binding peptide includes the amino acid sequence GGGYS (SEQ ID NO: 19)

Particular examples of heparin-binding peptides for use in the disclosed methods are shown in Table 1, below.

TABLE 1

| Peptide Name | Amino Acid Sequence | # of Amino Acids | MW | pI | Net charge |
|---|---|---|---|---|---|
| p5 | KAQKAQAKQAKQAQK AQKAQAKQAKQ (SEQ ID NO: 3) | 26 | 2836.2 | 10.85 | +8 |
| p5 + 14 | KAQKAQAKQAKQAQK AQKAQAKQAQKAQKA QKAQAKQAKQ (SEQ ID NO: 4) | 40 | 4345 | 11.04 | +12 |
| p5R + 14 | RAQRAQARQARQAQR AQRAQARQARQAQRA QRAQARQARQ (SEQ ID NO: 5) | 40 | 4681.2 | 13.04 | +12 |
| p5R | RAQRAQARQARQAQR AQRAQARQARQ (SEQ ID NO: 6) | 26 | 3060.4 | 12.85 | +8 |
| p10 | KGGKGGGKGGKGGGK GGKGGGKGGKG (SEQ ID NO: 7) | 26 | 2070.3 | 10.85 | +12 |
| p14 | AKYQKAQAKAQAKAQ RAQRAQARQARQAQR AQRAQARQARQ (SEQ ID NO: 8) | 41 | 4653.3 | 12.48 | +12 |

TABLE 1-continued

| Peptide Name | Amino Acid Sequence | # of Amino Acids | MW | pI | Net charge |
|---|---|---|---|---|---|
| P9 | KAQAKAQAKAQAKAQ AKAQAKAQAKAQAK (SEQ ID NO: 9) | 29 | 2935.4 | 10.85 | +8 |
| p42 | VYKVKTKVKTKVKTK VKT (SEQ ID NO: 10) | 18 | 2106.6 | 10.54 | +8 |

In some embodiments, the HS/heparin-binding polypeptides contain an amino acid sequence that is at least 95% identical to the amino acid sequence set forth as any one of SEQ ID NOS: 1-10, such as at least 95%, at least 96%, at least 97%, at least 98%, at least 99%, or 100% identical to the amino acid sequence set forth as any one of SEQ ID NOS: 1-10, for example at least 98%, at least 99%, or 100% identical to the amino acid sequence set forth as SEQ ID NO: 1, at least 98%, at least 99%, or 100% identical to the amino acid sequence set forth as SEQ ID NO: 2, at least 98%, at least 99%, or 100% identical to the amino acid sequence set forth as SEQ ID NO: 3, at least 98%, at least 99%, or 100% identical to the amino acid sequence set forth as SEQ ID NO: 4, at least 98%, at least 99%, or 100% identical to the amino acid sequence set forth as SEQ ID NO: 5, at least 98%, at least 99%, or 100% identical to the amino acid sequence set forth as SEQ ID NO: 6, at least 98%, at least 99%, or 100% identical to the amino acid sequence set forth as SEQ ID NO: 7, at least 98%, at least 99%, or 100% identical to the amino acid sequence set forth as SEQ ID NO: 8, at least 98%, at least 99%, or 100% identical to the amino acid sequence set forth as SEQ ID NO: 9, at least 98%, at least 99%, or 100% identical to the amino acid sequence set forth as SEQ ID NO: 10, or any combination of these peptides. In some instances it may be advantageous for the disclosed polypeptides to include heparin-binding polypeptides, such as 1, 2, 3, 4, or even more heparin-binding polypeptides. For example, 1, 2 3, 4, or more heparin-binding polypeptides that is at least 95% identical to the amino acid sequence set forth as any one of SEQ ID NOS: 1-10, such as at least 95%, at least 96%, at least 97%, at least 98%, at least 99%, or 100% identical to the amino acid sequence set forth as any one of SEQ ID NOS: 1-10 or any combination of such peptides.

In some embodiments a disclosed heparin-binding peptide may comprise or consist of from about 3 to about 55 amino acids. The peptides of the present invention may comprise or consist of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids.

The amino acids forming all or a part of a disclosed heparin-binding peptide may be stereoisomers and modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. The amino acids may be a D- or L-amino acids.

The disclosed heparin-binding peptides may also comprise one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Amino-propionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (AHyl), 3-Hydroxyproline (3Hyp), 4-Hydroxyproline (4Hyp), Isodesmosine (Ide), allo-Isoleucine (AIle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn). Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: Biochem J 268:249-262, 1990; and Toniolo C: Int J Peptide Protein Res 35:287-300, 1990; the teachings of all of which are incorporated herein by reference.

The heparin-binding peptides may be made by any technique known to those of skill in the art, including chemical synthesis or recombinant means using standard molecular biological techniques. The peptides may be synthesized in solution or on a solid support in accordance with conventional techniques. Various automatic synthesizers are commercially available and can be used in accordance with known protocols. (See, for example, Stewart and Young, Solid Phase Peptide Synthesis, 2d ed. Pierce Chemical Co., 1984; Tam et al., J. Am. Chem. Soc., 105:6442, 1983; Merrifield, Science, 232: 341-347, 1986; and Barany and Merrifield, The Peptides, Gross and Meienhofer, eds., Academic Press, New York, pp. 1-284, 1979, each is incorporated herein by reference in its entirety.)

Alternatively, recombinant DNA technology may be employed wherein a nucleotide sequence which encodes a peptide of the invention is inserted into an expression vector, transformed or transfected into an appropriate host cell, cultivated under conditions suitable for expression, and isolating the peptide.

In certain embodiments, the peptides may be obtained by isolation or purification. Protein purification techniques involve, at one level, the homogenization and crude fractionation of cells, tissue, or organ to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques.

Various chromatographic techniques include but are not limited to ion-exchange chromatography, gel exclusion chromatography, affinity chromatography, immuno-affinity chromatography, and reverse phase chromatography. A particularly efficient method of purifying peptides is fast performance liquid chromatography (FPLC) or even high performance liquid chromatography (HPLC).

The order of conducting the various purification steps may be changed, for example, or certain steps may be omitted, and still result in a suitable method for the preparation of a substantially purified peptide.

The peptides may be a part of a polypeptide or protein and may be produced by biochemical or enzymatic fragmentation of the polypeptide or protein. Accordingly, the peptides of the present invention may be (a) naturally-occurring, (b) produced by chemical synthesis, (c) produced by recombinant DNA technology, (d) produced by biochemical or enzymatic fragmentation of larger molecules, (e) produced by methods resulting from a combination of methods a through d listed above, or (f) produced by any other means for producing peptides.

During chemical synthesis, the peptides may be modified at its N- or C-terminus, thereby providing for improved stability and formulation, resistance to protease degradation, and the like. Examples of modifications of amino acids include pegylation, acetylation, alkylation, formylation, amidation. Moreover, various amino acids which do not naturally occur along the chain may be introduced to improve the stability of the peptides.

Also disclosed are nucleic acid molecules encoding these polypeptides. In some embodiments, the nucleic acid molecules include a nucleic acid sequence encoding an amino acid sequence at least 95% identical to the amino acids set forth as any one of SEQ ID NOS: 1-10, such as at least 95%, at least 96%, at least 97%, at least 98%, at least 99%, or 100% identical to the amino acids set forth as any one of SEQ ID NOS: 1-10. In the context of the compositions and methods described herein, a nucleic acid sequence that encodes at least one heparin-binding polypeptide, such as described above, is incorporated into a vector capable of expression in a host cell (for example an adenoviral vector), using established molecular biology procedures. For example nucleic acids, such as cDNAs, that encode at least one heparin-binding polypeptide can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell that includes a polynucleotide sequence that encodes at least one heparin-binding polypeptide can be found for example in Sambrook et ah, Molecular Cloning: A Laboratory Manual, 2d ed., Cold Spring Harbor Laboratory Press, 1989; Sambrook et ah, Molecular Cloning: A Laboratory Manual, 3d ed., Cold Spring Harbor Press, 2001; Ausubel et al., Current Protocols in Molecular Biology, Greene Publishing Associates, 1992 (and Supplements to 2003); and Ausubel et al, Short Protocols in Molecular Biology: A Compendium of Methods from Current Protocols in Molecular Biology, 4th ed., Wiley & Sons, 1999.

Typically, a polynucleotide sequence encoding at least one heparin-binding polypeptide is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRa, (3-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, dendritic cell-specific promoters, such as CD1 Ic, macrophage-specific promoters, such as CD68, Langerhans cell-specific promoters, such as Langerin, and promoters specific for keratinocytes, and epithelial cells of the skin and lung.

The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone. It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

C. Pharmaceutical Compositions

A disclosed heparin-binding polypeptide, such as any one of SEQ ID NOs; 1-10, can be administered by any means known to one of skill in the art (see Banga, A., "Parenteral Controlled Delivery of Therapeutic Peptides and Proteins," in Therapeutic Peptides and Proteins, Technomic Publishing Co., Inc., Lancaster, Pa., 1995) either locally or systemically, such as by intramuscular, subcutaneous, intraperitoneal or intravenous injection, but even oral, nasal, transdermal or anal administration is contemplated. In one embodiment, administration is by subcutaneous or intramuscular injection. To extend the time during which the peptide or protein is available, the peptide or protein can be provided as an implant, an oily injection, or as a particulate system. The particulate system can be a microparticle, a microcapsule, a microsphere, a nanocapsule, or similar particle. (see, e.g., Banga, supra).

Also disclosed are nucleic acid molecules encoding disclosed heparin-binding polypeptides, such as any one of SEQ ID NOs; 1-10. In some embodiments, the nucleic acid molecules include a nucleic acid sequence encoding an amino acid sequence at least 95% identical to the amino acids set forth as residues SEQ ID NOS: 1-10, such as at least 95%, at least 96%, at least 97%, at least 98%, at least 99%, or 100% identical to the amino acids set forth as any one of SEQ ID NOS: 1-10. These polynucleotides include DNA, cDNA and RNA sequences that encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. Freeman and Co., NY).

A nucleic acid encoding disclosed heparin-binding polypeptide, such as any one of SEQ ID NOs; 1-10, can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

In the context of the compositions and methods described herein, a nucleic acid sequence that encodes disclosed heparin-binding polypeptide, such as any one of SEQ ID NOs; 1-10, is incorporated into a vector capable of expression in a host cell, using established molecular biology procedures. For example nucleic acids can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell that includes a polynucleotide sequence that encodes disclosed heparin-binding polypeptide, such as any one of SEQ ID NOs; 1-10, can be found for example in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

The polynucleotides encoding a disclosed heparin-binding polypeptide, such as any one of SEQ ID NOs; 1-10, include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors can also be prepared encoding a disclosed heparin-binding polypeptide, such as any one of SEQ ID NOs: 1-10. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding disclosed heparin-binding polypeptide, such as any one of SEQ ID NOs: 1-10, is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

The disclosed heparin-binding polypeptides and nucleic acids encoding the same can be administered in vitro, ex vivo or in vivo to a cell or subject. Generally, it is desirable to prepare the compositions as pharmaceutical compositions appropriate for the intended application. Accordingly, methods for making a medicament or pharmaceutical composition containing the polypeptides, nucleic acids, adenovirus vectors or adenoviruses described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

The peptides of the present disclosure can be provided to a subject as part of a pharmaceutical composition where it is mixed with a pharmaceutically acceptable carrier. The purpose of a pharmaceutical composition is to facilitate administration of a compound to the patient. Pharmaceutical compositions can include an effective amount of the adenovirus vector or virus dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxypropylcellulose.

Dispersions also can be prepared in glycerol, liquid polyethylene glycols, and mixtures thereof and in oils. Under ordinary conditions of storage and use, these preparations contain a preservative to prevent the growth of microorganisms.

In some cases the compositions are administered to enhance the immune response, in such applications, the pharmaceutical composition is administered in a therapeutically effective amount. A therapeutically effective amount is a quantity of a composition used to achieve a desired effect in a subject. When administered to a subject, a dosage will generally be used that will achieve target tissue concentrations (for example, in lymphocytes) that has been shown to achieve an in vitro or in vivo effect.

Administration of therapeutic compositions can be by any common route as long as the target tissue (typically, the respiratory tract) is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers or other excipients.

The pharmaceutical compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well-known parameters.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders. Exemplary formulations can be found in U.S. Patent publication No. 20020031527, the disclosure of which is incorporated herein by reference. When the route is topical, the form may be a cream, ointment, salve or spray. Exemplary methods for intramuscular, intranasal and topical administration of the adenovirus vectors and adenoviruses described herein can be found, for example, in U.S. Pat. No. 6,716,823, which is incorporated herein by reference.

An effective amount of the pharmaceutical composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses. Generally, the pharmaceutical compositions described herein are administered for the purpose of stimulating and/or enhancing an immune response for example, an immune response against a viral antigen.

When administering a nucleic acid, facilitators of nucleic acid uptake and/or expression can also be included, such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, for example, *Liposomes: A Practical Approach*, RPC New Ed., IRL Press, 1990). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the trade name LIPOFECTIN®, and DOTAP (1,2-bis(oleyloxy)-3-(trimethylammonio)propane). See, for example, Felgner et al., *Proc. Natl. Acad. Sci. U.S.A.* 84:7413-7416, 1987; Malone et al., *Proc. Natl. Acad. Sci. U.S.A.* 86:6077-6081, 1989; U.S. Pat. Nos. 5,283,185 and 5,527,928, and International Publication Nos. WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, for example, International Publication No. WO 93/18759) and membrane-permeabilizing compounds such as GALA, Gramicidine S and cationic bile salts (see, for example, International Publication No. WO 93/19768).

Alternatively, nucleic acids (such as adenovirus vectors) can be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, for example, Jeffery et al., *Pharm. Res.* 10:362-368, 1993. Other particulate systems and polymers can also be used, for example, polymers such as polylysine, polyarginine, polyornithine, spermine, spermidine, as well as conjugates of these molecules.

Nucleic acids can be coated onto carrier particles (for example, core carriers) using a variety of techniques known in the art. Carrier particles are selected from materials that have a suitable density in the range of particle sizes typically used for intracellular delivery from an appropriate particle-mediated delivery device. The optimum carrier particle size will, of course, depend on the diameter of the target cells. Alternatively, colloidal gold particles can be used wherein the coated colloidal gold is administered (for example, injected) into tissue (for example, skin or muscle) and subsequently taken-up by immune-competent cells.

Tungsten, gold, platinum and iridium carrier particles can be used. Tungsten and gold particles are preferred. Tungsten particles are readily available in average sizes of 0.5 to 2.0 μm in diameter. Although such particles have optimal density for use in particle acceleration delivery methods, and allow highly efficient coating with DNA, tungsten may potentially be toxic to certain cell types. Gold particles or microcrystalline gold (for example, gold powder A1570, available from Engelhard Corp., East Newark, N.J.) will also find use with the present methods. Gold particles provide uniformity in size (available from Alpha Chemicals in particle sizes of 1-3 μm, or available from Degussa, South Plainfield, N.J. in a range of particle sizes including 0.95 μm) and reduced toxicity.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in a suitable particle delivery instrument, such as a gene gun. Alternatively, nucleic acid vaccines can be administered via a mucosal membrane or through the skin, for example, using a transdermal patch. Such patches can include wetting agents, chemical agents and other components that breach the integrity of the skin allowing passage of the nucleic acid into cells of the subject.

Therapeutic compositions that include a disclosed therapeutic agent can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (Science 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, Chem. Tech. 12:98-105, 1982, ethylene vinyl acetate (Langer et al., Id.) or poly-D-(-)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837, 028; 4,957,735; and 5,019,369; 5,055,303; 5,514,670; 5,413,797; 5,268,164; 5,004,697; 4,902,505; 5,506,206; 5,271,961; 5,254,342; and 5,534,496).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

DNA sequences encoding a disclosed heparin-binding polypeptide, such as any one of SEQ ID NOs; 1-10, can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a disclosed heparin-binding polypeptide, such as any one of SEQ ID NOs; 1-10, can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a disclosed heparin-binding polypeptide, such as any one of SEQ ID NOs; 1-10, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

EXAMPLES

The following examples further illustrate the invention but should not be construed as in any way limiting its scope.

I. Example 1—Heparan Sulfate-Binding Peptides for Blocking Viral Entry into Cells Materials and Methods
Peptide Synthesis and Purification Peptides were chemically synthesized and purified by high pressure liquid chromatography (HPLC [1100 series; Agilent]) by elution from a reverse-phase C3 matrix in a linear gradient of 0-50% acetonitrile in water with 0.05% trifluoroacetic acid. Peptide peaks were eluted from the column using a flow rate of 1 mL/min; 1-mL fractions were collected, peak fractions were pooled, and the mass was determined by MS using a single quadropole MS (Applied Biosystems). The purified peptides were lyophilized as 5 mg aliquots and we re-suspended in phosphate-buffered saline (150 mM NaCl, pH 7.2; PBS) before use. The re-suspended peptides were stored at 4° C. until use. In certain examples, such as indicated in Table 2 (below) the amino acid sequence GGGYS- was added to the N-terminus as a functional leader sequence during peptide synthesis.

Cells and Virus

Low passage-number cells (<20) were used for all the trials. Mouse embryonic fibroblast 10.1 (MEF 10.1 (45)) cells were used for all MCMV experiments. The cells were cultured in DMEM (Lonza, Rockland, Me.) supplemented with 10% Fetal Clone III serum (FCIII) (Hyclone, Logan, Utah), 1% Pen/Strep and 1% L-glutamine. Human foreskin fibroblast cells (HFF; obtained from ATCC) cultured in DMEM (Lonza, Rockland, Me.) supplemented with 10% Fetal Bovine Serum (FBS) (Hyclone, Logan Utah), 1% L-glutamine, and 1% sodium pyruvate, were used for experiments with HCMV. VERO cells (ATCC), were cultured in DMEM media supplemented with FBS, 1% sodium pyruvate 1% HEPES buffer and 1% antibiotic solution.

Murine Cytomegalovirus (MCMV) RM4503 was cultured in vitro in MEF 10.1 cells. The virus stock was titered using plaque assay (described below) and stored at −80° C. Human Cytomegalovirus (HCMV) TB40/E was obtained from (46, 47) and cultures in vitro in HFF cells. The virus stock was titered using plaque assay and stored at −80° C. HSV-1 and HSV-2 were cultured in vitro in VERO cells. The virus stock was titered using plaque assay and stored at −80° C.

Plaque Reduction Assay

Peptides were screened for their ability to reduce viral infection using a plaque reduction assay. Cells were cultured in 12-well (VERO) or 24-well culture plates (MEF 10.1 and HFF). When the cells reached ~80% confluence the media was removed and the cells washed once with PBS before addition of peptide. As a control, cells were incubated with PBS alone. After a 30 min of incubation with peptide in PBS, the virus was added and incubated for another 90 min (HSV and HCMV) or 60 min (MCMV). Following virus incubation the peptide/virus mixture was removed and replaced with 0.75% carboxy-methyl cellulose (Sigma Aldrich, St. Louis, Mo.)+complete media (CMC) or 0.5% agarose (Lonza, Rockland, Me.) in complete media. The plates were incubated at 37° C. in 5% $CO_2$ for 4 days when plaques began to develop, following which they were stained with Coomassie stain (AMRESCO, Solon, Ohio). Plaques were counted manually and data analyzed using Prism 5.0 (GraphPad Software, La Jolla, Calif.). Data were expressed as % plaques relative to the average number of plaques in the PBS-treated wells.

Interference of Peptide Mediated Reduction by Heparin

Peptide GGGY-p5+14 (SEQ ID NO: 25) (at 100 μM) was pre-incubated with heparin sodium salt (Acros Organics, NJ) at different concentrations for 1 h at 37° C. Following which the heparin/peptide mix was added to the cells and incubated for 30 min at 37° C. Following the incubation, the supernatant was aspirated and cells washed once with PBS to remove unbound/excess heparin or peptide. The cells were subsequently infected with ~100 pfu/well of MCMV. To test whether heparin treatment of cells interferes with virus infection, MEF 10.1 cells in a 24 well dish were pre-incubated with different concentrations of heparin for 1 hour and washed as described above. Following the pre-incubation infection was initiated as mentioned above. Finally to test the effect of heparin treatment on the infectivity of virus, MCMV was incubated with different concentration of heparin for 1hr before infecting cells. For all these treatments, the virus was removed 1hr post infection and cells overlaid with CMC. Plates were incubated for 4 days before staining and counting the plaques. Plaque reduction assay was performed as mentioned above.

Enzymatic Treatment of Cells

Heparinase I (cat. # H2519), Heparinase II (cat. # H6512), Heparinase III (cat. # H8891) and Chondroitinase ABC (cat. # C3667) were obtained from Sigma Aldrich (St. Louis, Mo.). MEF 10.1 cells in culture were treated with heparinase re-suspended in heparinase buffer (20 mM Tris-HCl, pH 7.5, 50 mM NaCl, 4 mM $CaCl_2$, and 0.01% BSA) at a concentration of 1 U/ml or chondroitinase re-suspended in chondroitinase buffer (50 mM Tris, pH 8.0, 60 mM sodium acetate and 0.02% bovine serum albumin) at a concentration of 1 U/ml for 1 h. at 37° C. As a control, cells were treated with enzyme buffer alone. Following incubation the enzyme solution was removed and cells were washed once with PBS to remove excess enzyme. Subsequently the cells were treated with peptide or infected with virus. The data was collected and analyzed as described previously.

Visualization of Bound Peptide

Coverslips with fixed MEF cells prepared, washed in PBS and blocked with 1% BSA/PBS for 5 min. Following a PBS wash the nuclei were stained by using Hoechst (Life Technologies Molecular Probes, Grand Island, N.Y.) 1:100 in $H_2O$— for 30 min at 37° C. Tissues were then blocked using a casein block solution (Scytek) for 5 min, AVIDIN/Biotin blocks (VECTOR, Burlingame, Calif.) for 20 min each at room temperature (RT) followed by a 5 min PBS wash. Biotinylated GGGY-p5+14 (SEQ ID NO: 25) or p5G (control) at 1.6 μg/mL in PBS was added and the tissues incubated overnight at 4° C. Following a PBS wash Alexa Fluor 594-conjugated streptavidin (Molecular Probes) was added at a 1:200 dilution in PBS for 1hr at RT. Cells were then permeabilized by addition of 0.2% Triton X-100 (Sigma) in PBS for 10 min at RT and washed with a solution of 1% BSA in PBS for 30 min. The cells were then stained with Alexa Fluor 488-conjugated phalloidin (Molecular Probes) 1:100 dilution of stock in 1% BSA/PBS, for 45 min. at RT to visualize cytoskeleton. Slides were cover-slipped using a fluorescent mounting medium (Dako, Carpinteria, Calif.) to minimize photobleaching.

Measuring Amount of Bound Peptide

MEF 10.1 Cells were grown in 24-well cell culture plates as described above. Each well was probed with 100 μL of biotinylated peptides at 1 μg/mL in cold DMEM/F12 with 0.1% BSA and incubated for one hour at 4° C. Following the incubation the cells were washed twice with ice cold PBS and fixed with 1.25% glutaraldehyde. Fixed samples were washed twice and stored in PBS for 24 hours. The samples were then blocked with 1% BSA in PBS and probed with 100 μL of Europium-conjugated streptavidin (Perkin-Elmer, Waltham, Mass.) in PBS/0.1% BSA for 30 minutes at RT. The plate was washed three times with PBS, enhancement solution added, and time resolved fluorescence measured on the Wallac Victor 3 (Perkin-Elmer).

Statistical Analysis

The data presented are the averages of triplicate measures from three or more experiments performed independently. Error bars represent the standard deviation (SD). Statistical significance was calculated using one tailed student's t test using GraphPad Prism. A p value <0.05 was considered statistically significant, *=p<0.05, =p<0.01, *=p<0.001, NS=non-significant.

Results

Screening of Peptides

Seven synthetic peptides based on the structure of peptide p5 were screened for their ability to reduce MCMV infection in vitro (Table 2).

TABLE 2

Primary sequence of peptides.

| Peptide | Sequence | Net Charge |
| --- | --- | --- |
| CGGY-p5 | CGGYSKAQKAQAKQAKQAQKAQKAQAKQAKQ (SEQ ID NO: 22) | +8 |

TABLE 2-continued

Primary sequence of peptides.

| Peptide | Sequence | Net Charge |
|---|---|---|
| CGGY-p5E | CGGYSEAQEAQEAEQAEQAQEAQEAQAEQAEQ (SEQ ID NO: 11) | −8 |
| CGGY-p5L | CGGYSLAQLAQALQALQAQLAQLAQALQALQ (SEQ ID NO: 12) | 0 |
| CGGY-p5G | CGGYSGAQGAQAGQAGQAQGAQGAQAGQAGQ (SEQ ID NO: 13) | 0 |
| GGGY-p5 | GGGYSKAQKAQAKQAKQAQKAQKAQAKQAKQ (SEQ ID NO: 23) | +8 |
| GGGY-p5R | GGGYSRAQRAQARQARQAQRAQRAQARQARQ (SEQ ID NO: 24) | +8 |
| GGGY-p5 + 14 | GGGYSKAQKAQAKQAKQAQKAQKAQAKQAKQA QKAQKAQAKQAKQ (SEQ ID NO: 25) | +12 |
| G2 | MPRRRRIRRRQK (SEQ ID NO: 14) | +8 |

In the initial screening assays all peptides were tested at a single concentration (500 μg/ml) using a plaque-reduction assay, in which mouse embryonic fibroblasts were incubated with the peptides for 30 min prior to the addition of virus. The polybasic peptides exhibited a range of viral inhibition up to >90% inhibition for peptide GGGY-p5+14 (SEQ ID NO: 25) (FIG. 1(A)). In contrast, the poly anionic, uncharged, and hydrophobic p5 variant peptides, CGGY-p5E (SEQ ID NO: 11), CGGY-p5G (SEQ ID NO: 13), and CGGY-p5L (SEQ ID NO: 12), respectively did not reduce MCMV infection (FIG. 1(A)). The presence of an N-terminal Cys residue (p5 is CGGYp5 (SEQ ID NO: 22) in FIG. 1(A)), which was originally generated to facilitate incorporation of the radionuclide $^{99m}$Tc) enhanced by 2-fold the inhibition of MCMV infectivity as compared to the GGGY N-terminal variant; however, the CGGYp5 was prone to self-aggregation and was therefore not further considered in this study.

Following the initial screen peptide GGGY-p5+14 (SEQ ID NO: 25) was selected for further analysis because it induced the greatest reduction in infection. Serial dilution of GGGY-p5+14 (SEQ ID NO: 25) peptide resulted in significant reduction in infection at concentrations >5 μg/mL (1 μM—FIG. 1(B)) with an IC$_{50}$ of 5.2 μM.

Structural Aspects and Insights into the Mechanism of Action

The secondary structure of peptide GGGY-p5+14 (SEQ ID NO: 25) was predicted by using the ITASSER software (28, 29) to be α-helical with the majority of the Lys residues aligned along one face of the peptide due to the heptad repeat in the protein sequence (30) (FIG. 1(C)).

To test the hypothesis that peptide GGGY-p5+14 (SEQ ID NO: 25) prevents MCMV infection by competing effectively for cell surface HSPG, biotinylated GGGY-p5+14 (SEQ ID NO: 25) was incubated with fibroblast cells in culture. Biotinylated peptide p5G served as a control. The GGGY-p5+14 (SEQ ID NO: 25) bound mouse fibroblasts in culture as evidenced by the red (Alexa 540) fluorescence stain associated with the cells (FIG. 1(D) left). In contrast, the electro-neutral peptide p5G did not bind to cells (FIG. 1(D), right), suggesting that fibroblast binding was dependent upon the presence of basic residues.

Peptide-Mediated Reduction of MCMV Infection Through Cell Surface HS Binding.

Figure 2:
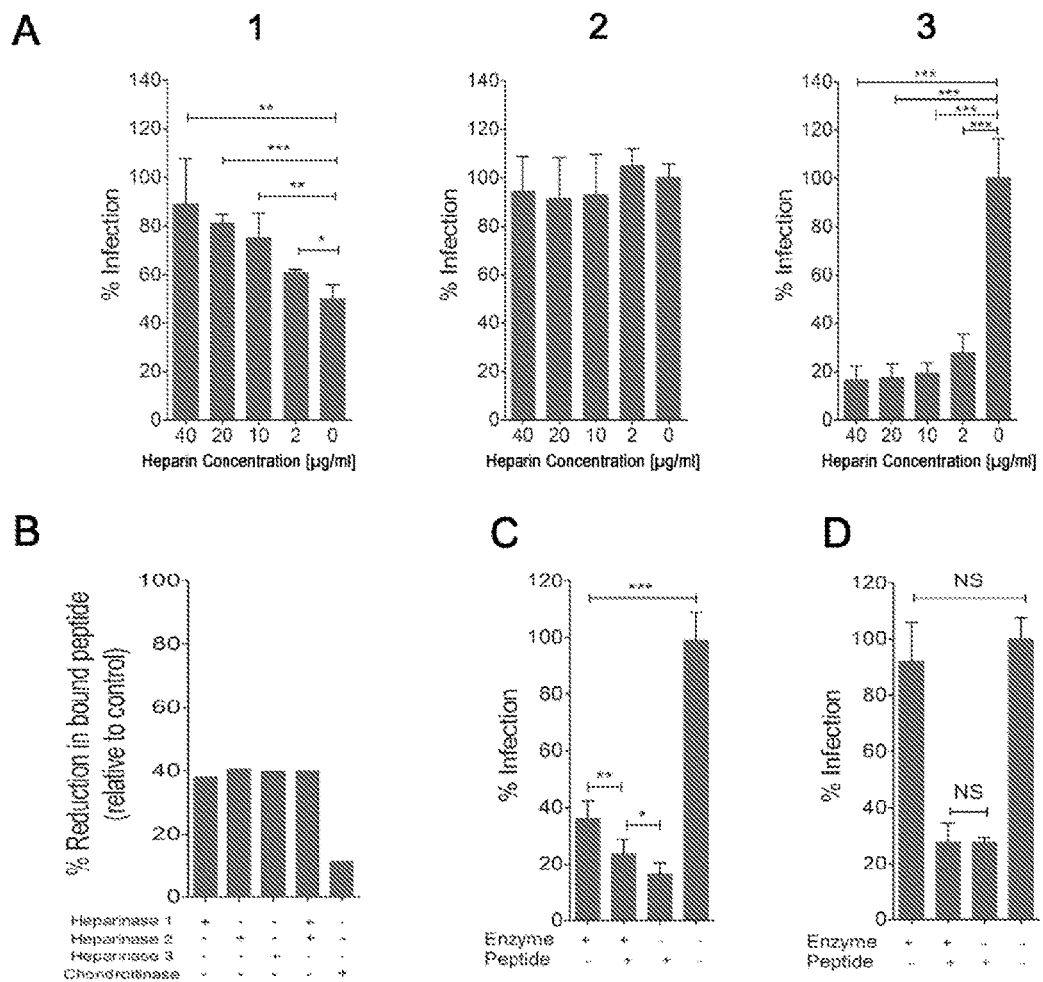
FIG. 2. Peptide-mediated anti-viral activity is dependent on cell surface heparan sulfate interactions. The effect of heparin on in vitro MCMV viral infectivity when (A1) pre-incubated with the peptide, (A2) incubated with the cells before adding virus, and (A3) pre-incubated with virus. (B) Heparinase treatment of MEF 10.1 cells reduced peptide binding to the cell surface (n=3). (C) The effect of heparinase (1 U/ml) or (D) chondroitinase (1 U/ml) treatment on the activity of peptide and MCMV infection measured by plaque reduction assay (mean+/−SD, n=3)

To test the role of HS-peptide interactions in the inhibition of MCMV infection, GGGY-p5+14 (SEQ ID NO: 25) was incubated with heparin. Pre-incubation of peptide with heparin before addition to the cells reduced its ability to inhibit MCMV infection in a dose-dependent manner (FIG. 2(A1)). In contrast, pre-incubation of the cells with heparin prior to virus addition did not alter MCMV infection (FIG. 2(A2)). Finally, pre-incubation of virus with heparin reduced virus infection >80% at heparin concentrations >2 μg/mL (FIG. 2(A3)).

To further identify the cell-surface peptide receptor(s), cells were treated with heparinase or chondroitinase enzymes. Treatment of cells with heparinase caused a ~40% reduction in the amount of bound peptide, whereas chondroitinase treatment resulted in a ~11% reduction (FIG. 2(B)). Since the peptide can bind both HS and CS, it is possible that the reduction of infection is mediated by direct competition for virus adsorption sites i.e. HS on the cell surface, stearic hindrance mediated by peptide bound to CS on the cell surface or both. Treatment of cells with heparinase (1 U/ml) led to a ~60% reduction in MCMV infectivity as expected, which was enhanced further by the addition of GGGY-p5+14 (SEQ ID NO: 25) leading to a ~80% reduction (FIG. 2(C)). At the same time addition of peptide alone showed greater reduction in infection as compared to when the peptide was added to heparinase treated cells (FIG. 2(C)). In contrast, treatment of cells with chondroitinase (1 U/ml) did not reduce MCMV infectivity, nor did it have any effect on the activity of the peptide (FIG. 2(D)). Pre-treatment of the virus with heparinase or chondroitinase prior to addition to fibroblasts did not alter its infectivity.

Peptide Competes for Virus Adsorption to the Cell Surface

In the infectivity assays described above the peptide and virus were co-incubated with the cells. Therefore to ensure the peptide was not directly inactivating the virus, MCMV was incubated with 100 μM (~20× the IC$_{50}$) peptide at 37° C. for 1 h, diluted to an ineffective peptide concentration (1 μM) and fibroblast infection rates measured. There was no reduction in MCMV infection under these conditions, whereas addition of peptide and virus simultaneously to the cells showed significant reduction in infection (FIG. 3A).

Figure 3:
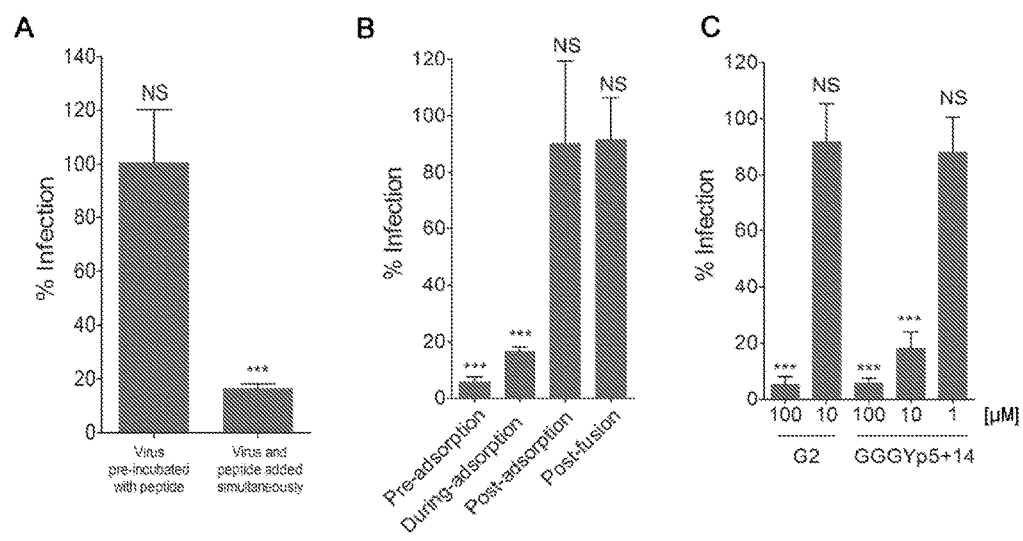
FIG. 3. Peptide p5+14 blocked adsorption of MCMV. (A) Comparison of infectivity of MCMV either pre-incubated with peptide or added to cells simultaneously with the peptide (B) Peptide GGGY-p5+14 (SEQ ID NO: 25) effectively inhibited infection of MCMV when added before the adsorption phase of viral entry. (C) Comparison of GGGY-p5+14 (SEQ ID NO: 25) with peptide G2 for preventing MCMV viral infection in vitro. All data are mean+/−SD, n=3.

To determine at which stage of the MCMV entry cycle the peptide interferes, four different peptide treatment protocols were tested, 1) 30 min. prior to infection (pre-adsorption) 2) simultaneously with virus (during adsorption) 3) after letting the virus adsorb to the cells at 4° C. for 1hr (post adsorption) or 4) after allowing the virus to fuse with the cell membrane at 37° C. for 1hr (post fusion) (FIG. 3(B)). Addition of the GGGY-p5+14 (SEQ ID NO: 25) peptide before or in conjunction with virus addition to the cells resulted in >80% infection; however, when peptide was added after the adsorption or fusion phase of viral entry, no significant reduction in plaque formation was observed (FIG. 3(B)).

The efficacy of infection inhibition by peptide GGGY-p5+14 (SEQ ID NO: 25) was compared to the recently reported inhibitor, peptide G2 (Table 2). Both peptides effectively inhibited MCMV infection at 100 μM. However, peptide GGGY-p5+14 (SEQ ID NO: 25) caused a >80% reduction in infection at 10 μM at which concentration peptide G2 was ineffective (FIG. 3(C)).

p5+14 Inhibition of Human Herpes Virus Infection

Figure 4:
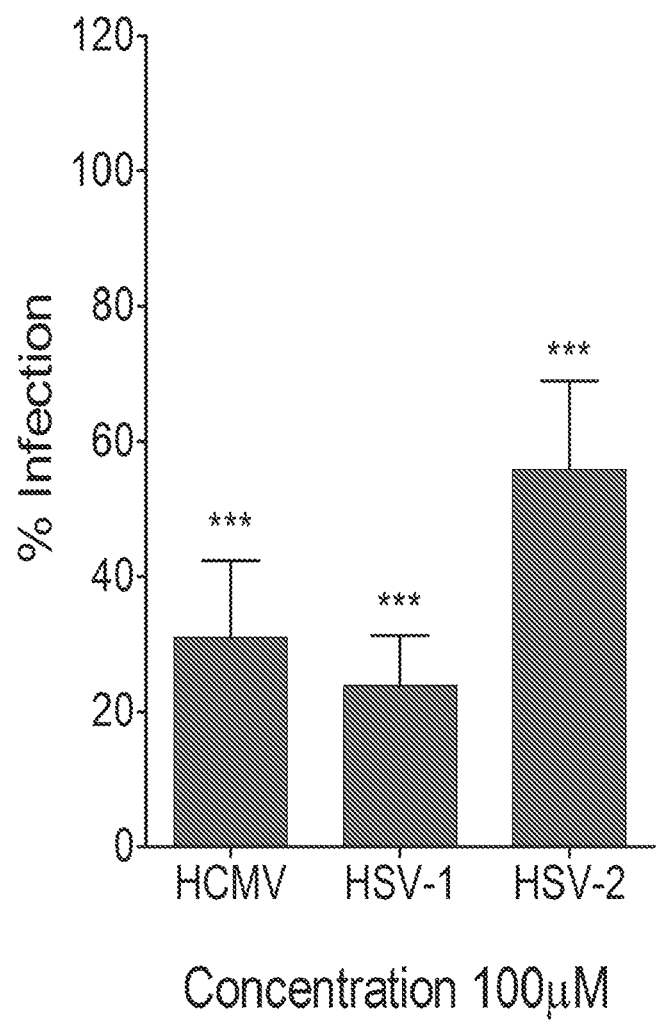
FIG. 4. Peptide p5+14 inhibits HCMV and HSV virus infections in vitro. Peptide GGGY-p5+14 (SEQ ID NO: 25) (100 µM) effectively inhibited HCMV, HSV-1 or HSV-2 viral infection (Mean+/−SD, n=3).

Addition of peptide GGGY-p5+14 (SEQ ID NO: 25) in a human CMV (HCMV) infectivity assay resulted in a ~80% reduction of infection (FIG. 4). Similar inhibition was observed when herpes simplex virus (HSV) 1 was tested; however, reduction of HSV 2 infection was less effective (~40% reduction).

DISCUSSION

Cytomegalovirus infection is a significant clinical problem in infants and immunodeficient populations. Current anti-viral therapies can cause significant organ toxicity and viral resistance is becoming apparent. In this study, a panel of synthetic peptides, known to bind hypersulfated GAGs, was examined for their ability to bind cultured murine fibroblasts and thereby inhibit the infection of herpes viruses—using MCMV as the model system. The ultimate goal is the identification of novel, synthetic anti-viral peptides. Of the seven peptides evaluated in this study, peptide GGGY-p5+14 (SEQ ID NO: 25) demonstrated effective inhibition of MCMV infection and reduced infection of both HCMV and HSV (HSV-1 and 2) (FIG. 4), suggesting the broader applicability of GAG-binding synthetic peptides for inhibiting virus-cell interactions. We established that the peptide effectively competed for adsorption of CMV to susceptible cells, thereby reducing infection. We also demonstrated that the peptide did not have any direct neutralizing effect on the virus itself.

The p5-related peptides are synthetic, polybasic reagents with a predicted α-helical secondary structure. The heptad amino acid repeat—KAQKAQA—(SEQ ID NO: 20) positions the Lys residues along one face of the helix. This structural feature was engineered and intended to facilitate an interaction with linear, sulfated GAG molecules, notably heparin (30, 31). Due to their ability to preferentially bind hypersulfated GAGs these peptides have been used to effectively target and image tissue amyloid deposits (24, 25), which contain hypersulfated HS and possibly CS proteoglycans (32). Remarkably, when radiolabeled CGGY-p5 (SEQ ID NO: 22) (and GGGY-p5+14) peptide was injected in disease-free mice there is no evidence of peptide binding to GAGs expressed in healthy organs or tissues, with the exception of the proximal renal tubules, where re-adsorption occurs during catabolism (24). Therefore, without being bound by any particular theory, we hypothesize that the linear positive charge on peptide GGGY-p5+14 (SEQ ID NO: 25) facilitates the binding to negatively-charged PGs on the cell surface, inhibits viral binding to the same site, and thereby mediates antiviral activity. This is supported by the fact that peptides with the same net positive charge exhibit differential anti-viral effects that are consistent with the peptide affinity for the GAGs (and amyloid). Thus, peptide GGGY-p5R (SEQ ID NO: 24) (+8 charge), which has a higher affinity for heparin (30) and amyloid (33) as compared to peptide p5 (+8 charge) (as noted above, p5 is CGGY-p5 (SEQ ID NO: 22) in FIG. 1(A)), blocks viral infection 4-fold better (FIG. 1(A)). These data suggest that peptide p5+14 (SEQ ID NO: 4) and similar reagents effect anti-viral activity by competing for virus binding to GAGs on the cell surface. Based on the known restricted reactivity of peptides CGGY-p5 (SEQ ID NO: 22) and GGGY-p5+14 (SEQ ID NO: 25) in vivo, the data presented in this study using GGGY-p5+14 (SEQ ID NO: 25) further suggests that the CMV may preferentially bind hypersulfated GAGs on the cell surface of cultured fibroblasts, which may differ from the ubiquitously-expressed GAGs found in tissue HSPG and CSPG proteins in vivo.

An alternative mode of action for the peptides may involve internalization of the shared peptide and virus GAG ligand. For example, cell penetrating peptides that are rich in arginine or lysine containing, are known to bind HS on the cell surface resulting in internalization of the complex (34, 35). This mechanism may be used to deliver drugs or diagnostic/therapeutic nanoparticles (36-38). It remains to be evaluated whether peptide p5+14 binding to the cell surface ligand results in internalization of the peptide-ligand complex (those studies are underway). Should this be the case it would provide an alternative explanation for the ability to inhibit CMV infection and provide data in support of using peptide p5+14 (SEQ ID NO: 4) and similar peptides as disclosed herein as reagents for delivery of intracellularly-active payloads.

Recent work by Tiwari et al. (39) and Borst et al. (40) identified HS-reactive, anti-viral peptides G2 and CYVIP (SEQ ID NO: 21) from a phage library screen and from human hemofiltrate, respectively. Although G2 peptide has been successfully synthesized and evaluated, the synthesis of CYVIP (SEQ ID NO: 21) was not facile. In concordance with our findings, the positive charge of these peptides was critical for their anti-viral activity in both these studies. Notably, peptide GGGY-p5+14 (SEQ ID NO: 25) was more effective at inhibiting MCMV infection of mouse fibroblasts in vitro as compared to peptide G2 (FIG. 3(C)). The $IC_{50}$ value for GGGY-p5+14 (SEQ ID NO: 25) was lower than the reported values for both G2 and CYVIP (SEQ ID NO: 21) peptides. Although these peptides have a similar mode of action, there is significant difference in the size and charge distribution. The length and spatial arrangement of charged amino acids affect binding to heparin (30), HS-laden amyloid (41), and cells surface HS (35). Systematic evaluation of the physical, electrochemical, and structural characteristics that contribute to anti-viral activity will aid in the design of next generation therapeutic reagents.

In this study we show that peptide GGGY-p5+14 (SEQ ID NO: 25), which without the leader sequence corresponds to p5+14 (SEQ ID NO: 4), exhibited significant anti-viral activity against HCMV, HSV-1 and 2 albeit to a lesser degree in the case of the latter. Even though we propose a similar mode of action against each virus (i.e. blocking of viral adsorption to cell-surface HS) the difference in the peptide p5+14 efficacies is intriguing. Possible differences in the gB proteins of these viruses could lead to preferential use of GAGs to adsorb to the cell surface (42) and could lead to differences in the efficacy of the peptide against the two HSV serotypes. Indeed, the fine structure and distribution of HS GAGs can be different based on the cell type under study (43, 44). It is possible, indeed likely, that the p5+14 peptide (and similar reagents) exhibit preferential binding to GAGs that could lead to differences in cell-surface binding and ant-viral efficacy. Notably, peptide p5 was shown by circular dichroism measurements to preferentially bind heparin and adopt an α-helical configuration as compared to HS, CS (A and C), dermatan sulfate, and hyaluronic acid (31).

It has previously been shown by using SPECT imaging and micro-autoradiography that the "ligand" bound by peptides p5 and p5+14 has a restricted distribution in vivo. The peptides do not bind cellular GAGs or those in the extracellular matrix of healthy tissues. This observation, taken together with the fact that these peptides compete with herpes viruses for binding to cells in culture suggests that viruses may preferentially bind to a subset of HS in vivo that is characterized by a high sulfation pattern, i.e. electrochemically more reminiscent of heparin. This remains to be established in vivo.

It is well known that CMV and other herpes viruses establish latency within the host, which is dependent on virus entry and infection of the host cells. Preventing the entry of the virus using competitive peptides could potentially reduce the ability of virus to establish latency in the host. Given this, even though HS on cell surface is a lucrative target for developing anti-virals, reports targeting this pathway during viral infections in vivo are scarce (39) likely due to the fact that HS is ubiquitous and involved in numerous critical cell-signaling pathways. Thus, peptides such as p5+14 (SEQ ID NO: 4) that specifically targeted heparin-like HS may afford selective viral competition in vivo without detrimentally affecting biological signaling through HS.

Figure 5:
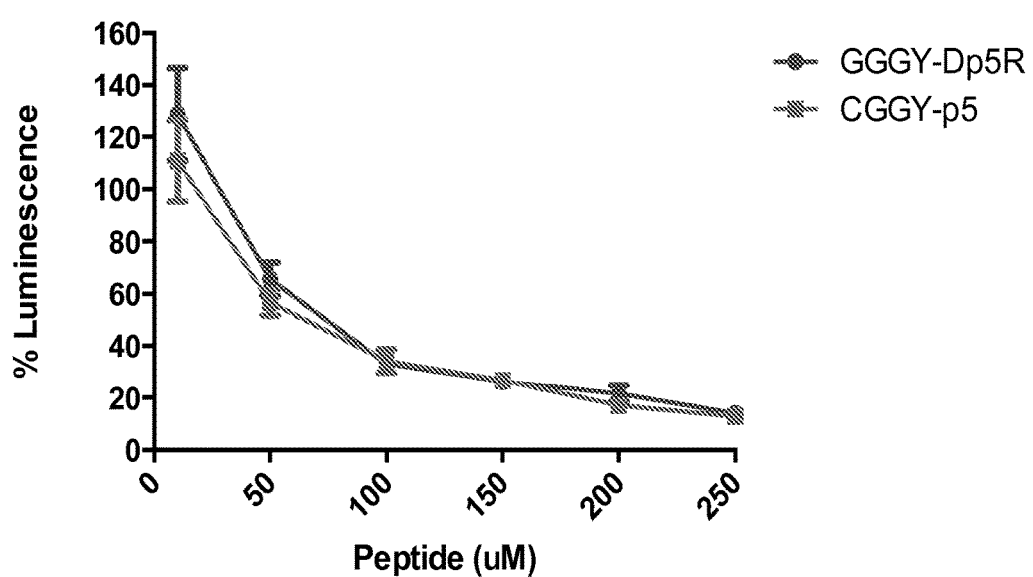
FIG. 5. The $IC_{50}$ values for p5 and Dp5R. The peptides, CGGY-p5 (SEQ ID NO: 22) and GGGY-Dp5R (SEQ ID NO: 24, D form), were added to MRC-5 cells 30 min prior to the addition of HCMV expressing luciferase at various concentrations to determine the $IC_{50}$. All data sets are representative of three independent experiments with at least three repeats ±SD.
Figure 6:
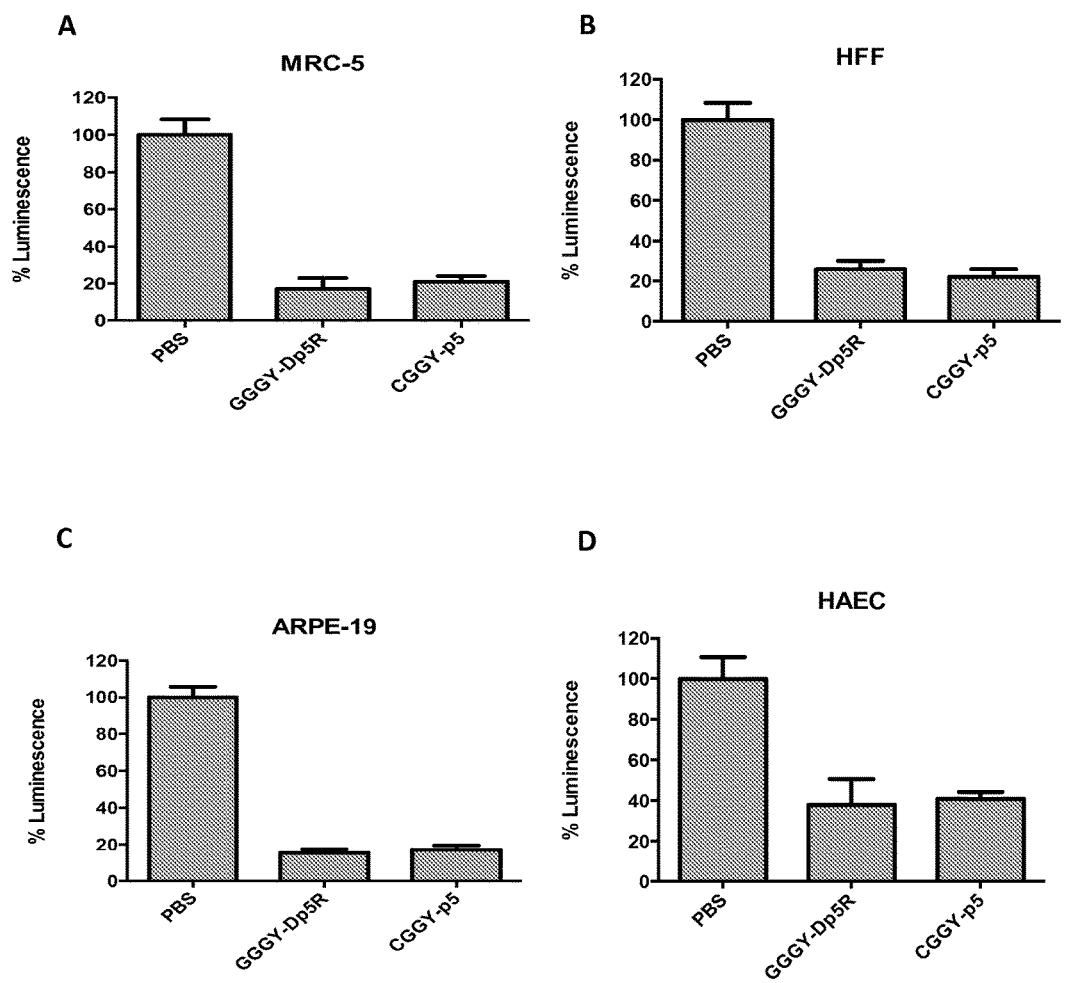
FIG. 6. The efficacy of peptides on different cell types. (A) MRC-5 cells treated with CGGY-p5 (SEQ ID NO: 22) and GGGY-Dp5R (SEQ ID NO: 24, D form) show ~80% reduction in luminescence. (B) HFF cells treated with CGGY-p5 (SEQ ID NO: 22) and GGGY-Dp5R (SEQ ID NO: 24, D form) show ~75% reduction in luminescence. (C) ARPE-19 cells treated with CGGY-p5 (SEQ ID NO: 22) and GGGY-Dp5R (SEQ ID NO: 24, D form) show ~85% reduction in luminescence. (D) HAEC cells treated with CGGY-p5 (SEQ ID NO: 22) and GGGY-Dp5R (SEQ ID NO: 24, D form) show ~60% reduction in luminescence. All data sets are representative of three independent experiments with at least three repeats ±SD.
Figure 7:
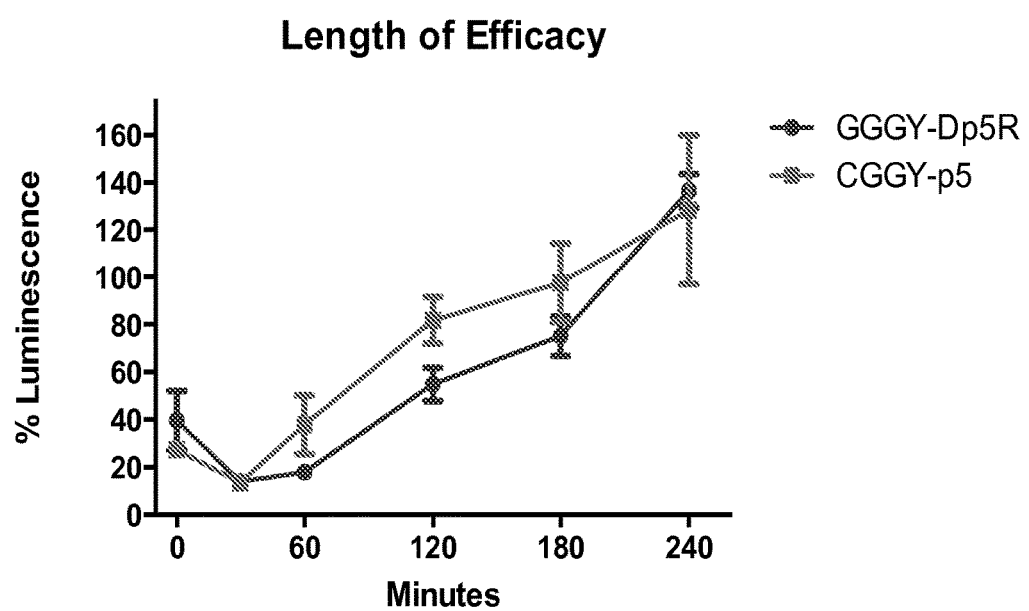
FIG. 7. p5 and Dp5R duration of efficacy. Peptide was added to MRC-5 cells 0 min, 30 min, 60 min, 120 min, 180 min, 240 min before virus was added to determine the length of time the peptide would reduce HCMV infection. The GGGY-Dp5R (SEQ ID NO: 24, D form) peptide showed a 50% reduction in infection at 2 hr, while the CGGY-p5 (SEQ ID NO: 22) was less effective after 1 h. Symbols represent the average of 3 replicates ±SD and is representative of two separate experiments.
Figure 8:
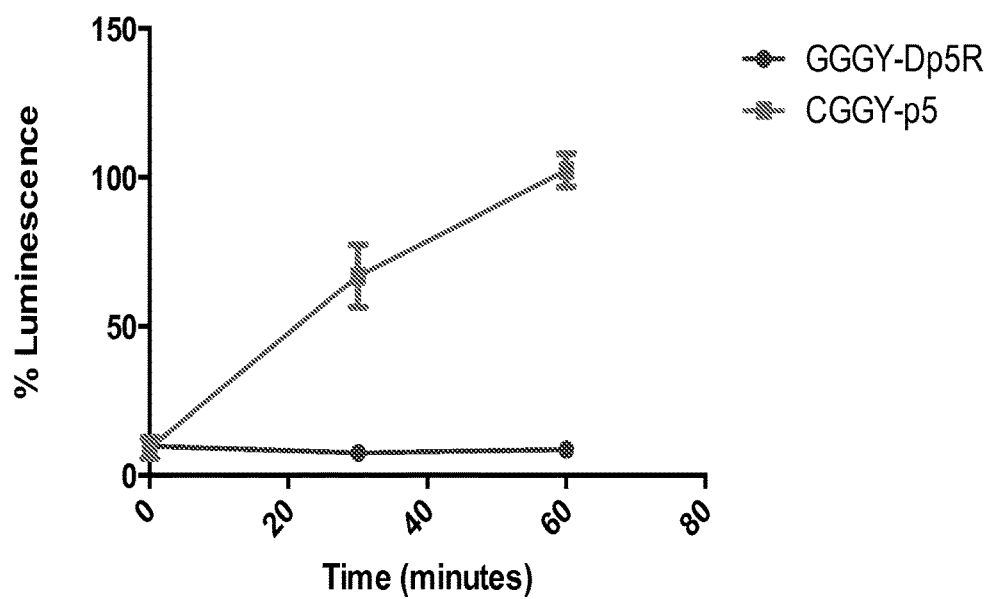
FIG. 8. Proteolytic stability of p5 and Dp5R. 200 µM of each peptide, CGGY-p5 (SEQ ID NO: 22) and GGGY-Dp5R (SEQ ID NO: 24, D form), was incubated with 200 µg/ml of trypsin for 30 minutes and 60 minutes then added to MRC-5 cells 30 minutes prior to the addition of virus. Data is representative of three separate experiments with three repeats ±SD.

II. Example 2—Proteolytically Stable D-Form Peptide and Inhibition in Human Cytomegalovirus Infection Materials and Methods
Virus
A recombinant luciferase-expressing Towne strain of HCMV was used for each experiment. To obtain the virus, the virus was cultured in vitro on HFF cells. The virus was titered using a standard plaque assay.
Cells
Cells were cultured according to methods known to those of skill in the art. Briefly, human fetal lung fibroblasts (MRC-5, ATCC) were cultured in minimum essential media (MEM, HyClone) supplemented with fetal bovine serum (FBS, HyClone), and L-glutamine. Human foreskin fibroblasts (HFF, ATCC) were cultured in dulbecco's modified eagle medium (DMEM, GE HyClone) supplemented with FBS, L-glutamine and sodium pyruvate. Human aortic endothelial cells were cultured in EGM-2 Bullet Kit (Lonza) supplemented with FBS. Human retinal pigment epithelia cells (ARPE-19) were cultured in DMEM and Hams F12 medium (Lonza) and supplemented with FBS.
Luciferase Assay
Efficacy of viral reduction was measured using a luciferase assay with HCMV expressing luciferase virus. Cells were cultured in a 24-well plate until they reached ~80% confluency. The cells were washed with phosphate buffered saline (PBS) then treated with peptide. The control cells were treated with PBS supplemented with FBS. After peptide incubation, virus was added (100 RLU for MRC-5, HFF and 1000 RLU for HAEC, ARPE-19) for 1 h. After incubation with virus, the media was removed and fresh media was added to the wells. The plates were incubated at 37° C. for 3 days (MRC-5) or 5 days (HFF, ARPE-19 and HAEC). After incubation the cells were washed with PBS, treated with Passive Lysis Buffer (PLB, Promega E1500), detached using a rubber scraper, vortexed and centrifuged. The supernatant containing the luciferase protein was added in equal parts to Luciferase Assay Reagent (LAR, Promega E1500) into a 96-well white opaque plate (Costar). After the addition of LAR to the supernatant the luminescence was quantified using a plate reader (BioTek). Data was normalized to uninfected control using Graph Pad Prism.
MTS Assay
The toxicological profile of p5 and Dp5R (the D-form of p5) was determined using an MTS assay (Promega, #G3582) on MRC-5 cells. 5000 MRC-5 cells were plated 18 h before the addition of peptide. Peptide was added to cells at 400 μM, 200 μM and 100 μM. The negative control received media alone and the positive control received a 1% Triton-x 100 solution (Fisher Scientific). Peptide and media was incubated with the cells for 24 hours. After incubation the Cell Titer AQ$_{ueous}$ One Solution Reagent was added to the peptide/media solution at a 5:1 (peptide:reagent) ratio. The cells were incubated with the reagent at 37° C. for 1 h. The absorbance was recorded at 490 nm using a plate reader (BioTek). Data was analyzed using GraphPad Prism.
Results
Determining the IC$_{50}$ for p5 and Dp5R
The IC$_{50}$ for Dp5R (i.e., the D form of peptide GGGY-p5R (SEQ ID NO: 24)) was unknown and the IC$_{50}$ for p5 (i.e., CGGY-p5 (SEQ ID NO: 22)) had previously been determined using plaque assay (48). Both peptides were tested using the HCMV expressing luciferase virus. The peptide was tested on MRC-5 cells at the following concentrations: 10 μM, 50 μM, 100 μM, 150 μM, 200 μM, 250 μM. The IC$_{50}$ for p5 is ~60 μM and the IC$_{50}$ for Dp5R is ~75 μM (FIG. 5). The IC$_{50}$ values for both the peptides are relatively similar suggesting that the peptides have comparable inhibition of viral infection in vitro.
Peptide Efficiency on Different Cell Types
CMV is known to infect a wide range of cell types. Hence, more beneficial therapeutics to treat CMV infection should be effective on multiple cell types. Both the D and L peptide types (i.e., GGGY-Dp5R (SEQ ID NO: 24, D form) and CGGY-p5 (SEQ ID NO: 22), respectively) were tested for their ability to reduce HCMV infection in different cell types. Four cell types were used: MRC-5 and HFF (fibroblasts), ARPE-19 (epithelial cells) and HAEC (endothelial cells) (FIG. 6). The percent luminescence for both peptides on MRC-5 cells is ~20% (FIG. 6(A)), 25% on HFF cells (FIG. 6(B)), 15-20% on ARPE-19 cells (FIG. 6(C)), and 40% on HAEC cells (FIG. 6(D)). The percent reduction of HCMV infection on different cell types is comparable between the L-form, p5, and the D-form, Dp5R. Both forms of the p5 peptides thus reduce HCMV infection.
Duration of Anti-CMV Efficacy of p5 and Dp5R
Without being bound by any particular theory, it is expected that improved inhibition of viral infection will occur when heparin sulfate binding peptides stay bound to the cell types vulnerable to infection for an extended period of time. Hence, the length of time that CGGY-p5 (SEQ ID NO: 22) and GGGY-Dp5R (SEQ ID NO: 24, D form) reduce HCMV infection was determined by adding virus for longer than the 30 minutes used in previous experiments. Peptide was added to cells then virus was added at the following time points after the addition of peptide: 0 min, 30 min, 60 min, 120 min, 180 min, and 240 min. For times longer than 30 minutes, peptide was removed and media was added until the cells were treated with virus later (FIG. 7). Both p5 and Dp5R peptides show approximately 50% or more reduction at 60 minutes. However, p5 is largely ineffective at reducing HCMV infection beyond 1 h. The Dp5R peptide is able to reduce virus infection at 2 hrs. But after 2 hrs, both the p5 and Dp5R lose their efficacy. Without wishing to be bound by any particular theory, the increased longevity of the Dp5R peptide might be attributable to the more stable D-form.
Proteolytic Stability of p5 and Dp5R
As described herein, GGGY-Dp5R (SEQ ID NO: 24, D form) was shown to bind longer to cells than CGGY-p5 (SEQ ID NO: 22). Without wishing to be bound by any particular theory, this increased binding could be due to proteolytic stability of the D-form. Trypsin was thus used to test the proteolytic stability of p5 and Dp5R. More particularly, each peptide was incubated at 37° C. for 30 minutes and 60 minutes with 200 μg/ml of trypsin then added to cells 30 minutes before the addition of virus. Dp5R retained its ability to reduce infection after 60 minutes of incubation with trypsin (FIG. 8). The p5 peptide was only able to reduce viral infection in cells when it had not been treated with trypsin. Hence, these data suggest that the proteolytic stability may improve the function of anti-viral peptides, inasmuch as peptide-based compositions, as described herein, will likely encounter proteases in vivo.

Cell Viability Assay

Figure 9:
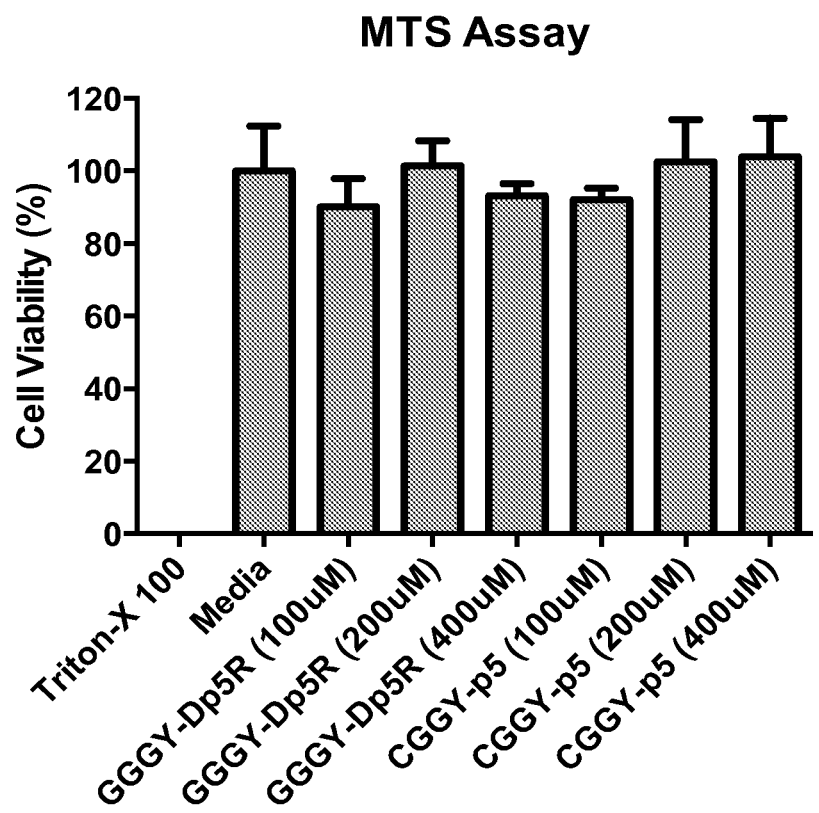
FIG. 9. Cell viability assay. MRC-5 cells were added to a 96-well plate and allowed to attach. Each peptide was added at 100 µM, 200 µM, and 400 µM and incubated at 37° C. for 24 hours before the addition of 96 Aqueous One Solution (Promega) at a 5:1 (media:reagent) ratio. Absorbance was recorded at 490 nm using a plate reader (BioTek). Data was analyzed using GraphPad Prism. Data are representative of three separate experiments with three or more repeats ±SD.

In order to determine if either CGGY-p5 (SEQ ID NO: 22) or GGG-Dp5R is toxic to cells, an MTS assay was performed. Cells were treated with peptide and media, Triton-x 100 (positive control) or media alone (negative control) for 24 hours (FIG. 9). As shown in FIG. 9, the peptides are not toxic to cells, with results being comparable to the negative control. Cell viability remained above 90% for each peptide at all concentrations tested. The toxicological profile of Dp5R thus strengthens the peptide's potential as a therapeutic to treat HCMV infection.

DISCUSSION

Currently, HCMV infection in immunocompromised individuals is treated using anti-viral drugs that target virus replication. A problem that arises, however, is drug resistance. There are a growing number of HCMV resistant cases to commonly used anti-virals (9-11).

As described herein, an approach to treating HCMV would thus be to develop a therapeutic drug that acts on the host rather than directly on the virus. The L-form of the p5-related peptide, p5+14 (SEQ ID NO.: 4), was tested in vitro and shown to be most potent at inhibiting CMV infection. In addition to identifying peptides that inhibit viral infection, as described herein, we hypothesized that a D-form of the heparin reactive peptide may be more stable, such as when incubated with a protease. By increasing stability, for example, the length of the inhibitory effect of the peptide may be increased in vivo. The data provided herein show that, while p5 and Dp5R work similarly in vitro, Dp5R (which, without the GGGY-leader sequence, corresponds to the same primary sequence as in SEQ ID NO: 6) is more proteolytically stable. This stability may potentially allow this heparin reactive peptide to work more efficiently in vivo.

REFERENCES

Each of the following documents are hereby expressly incorporated by reference in their entirety:
1. Schleiss M R (Pediatric Cytomegalovirus Infection (Web MD professional).
2. Gerna G, Baldanti F, & Revello M G (2004) Pathogenesis of human cytomegalovirus infection and cellular targets. *Human immunology* 65(5):381-386.
3. Pass R F (2001) Cytomeaglovirus. *Fields Virology 4th edn*, eds Knipe D M & Howley P M (Lippincott-Raven, Philadelphia), 4th Ed Vol 2.
4. Tania C & Rajiv K (2009) Immunobiology of human cytomegalovirus: from bench to bedside. *Clinical microbiology reviews* 22(1):76.
5. Sung H & Schleiss M R (2010) Update on the current status of cytomegalovirus vaccines. *Expert review of vaccines* 9(11):1303-1314.
6. Griffiths P, et al. (2013) Desirability and feasibility of a vaccine against cytomegalovirus. *Vaccine* 31 Suppl 2:203.
7. Ramanan P & Razonable R R (2013) Cytomegalovirus Infections in Solid Organ Transplantation: A Review. *Infection & chemotherapy* 45(3):260-271.
8. Biron K (2006) Antiviral drugs for cytomegalovirus diseases. *Antiviral research* 71(2-3):154-163.
9. Li F, et al. (2007) Incidence and clinical features of ganciclovir-resistant cytomegalovirus disease in heart transplant recipients. *Clinical infectious diseases: an official publication of the Infectious Diseases Society of America* 45(4):439-447.
10. Lurain N S & Chou S (2010) Antiviral drug resistance of human cytomegalovirus. *Clinical microbiology reviews* 23(4):689-712.
11. Le Page A K, et al. (2013) Clinical aspects of cytomegalovirus antiviral resistance in solid organ transplant recipients. *Clinical infectious diseases: an official publication of the Infectious Diseases Society of America* 56(7):1018-1029.
12. Limaye A P, Corey L, Koelle D M, Davis C L, & Boeckh M (2000) Emergence of ganciclovir-resistant cytomegalovirus disease among recipients of solid-organ transplants. *Lancet* 356(9230):645-649.
13. Esko J & Lindahl U (2001) Molecular diversity of heparan sulfate. *The Journal of clinical investigation* 108(2):169-173.
14. Anonymous (2001) Molecular diversity of heparan sulfate. *Journal of Clinical Investigation* 108(2):169173.
15. Anonymous (2002) Heparin and heparan sulfate: structure and function. *Natural Product Reports* 19(3):312331.
16. Sasisekharan R & Venkataraman G (2000) Heparin and heparan sulfate: biosynthesis, structure and function. *Current opinion in chemical biology*.
17. Merton B, et al. (1999) FUNCTIONS OF CELL SURFACE HEPARAN SULFATE PROTEOGLYCANS. *Annual Review of Biochemistry* 68(1):729777.
18. LJUNGH TWaA (1984) Glycosaminoglycan-binding microbial proteins in tissue adhesion and invasion: key events in microbial pathogenicity. *Journal of medical microbiology* 18(3):438438.
19. Watanabe N, et al. (2004) Glypican-1 as an Abeta binding HSPG in the human brain: its localization in DIG domains and possible roles in the pathogenesis of Alzheimer's disease. *FASEB journal: official publication of the Federation of American Societies for Experimental Biology* 18(9):1013-1015.
20. Compton T, Nowlin D M, & Cooper N R (1993) Initiation of human cytomegalovirus infection requires initial interaction with cell surface heparan sulfate. *Virology* 193(2):834-841.
21. Shieh M, WuDunn D, & Montgomery . . . R (1992) Cell surface receptors for herpes simplex virus are heparan sulfate proteoglycans. *The Journal of cell* . . . .
22. Deepak S & Patricia G S (2001) Herpesviruses and heparan sulfate: an intimate relationship in aid of viral entry. *Journal of Clinical Investigation* 108.
23. Liu J & Thorp S (2002) Cell surface heparan sulfate and its roles in assisting viral infections. *Medicinal research reviews* 22(1):1-25.
24. Wall J, et al. (2011) In vivo molecular imaging of peripheral amyloidosis using heparin-binding peptides. *Proceedings of the National Academy of Sciences of the United States of America* 108(34):94.
25. Wall J, et al. (2012) Comparative analysis of peptide p5 and serum amyloid P component for imaging AA amyloid in mice using dual-isotope SPECT. *Molecular imaging and biology: MIB: the official publication of the Academy of Molecular Imaging* 14(4):402-407.
26. Wall J S, et al. (2011) SPECT imaging of peripheral amyloid in mice by targeting hyper-sulfated heparan sulfate proteoglycans with specific scFv antibodies. *Nuclear medicine and biology* 39(1):65-75.

27. Smits N C, et al. (2010) The heparan sulfate motif (GlcNS6S-IdoA2S)3, common in heparin, has a strict topography and is involved in cell behavior and disease. *The Journal of biological chemistry* 285(52):41143-41151.
28. Roy A, Kucukural A, & Zhang Y (2010) I-TASSER: a unified platform for automated protein structure and function prediction. *Nature protocols* 5(4):725-738.
29. Zhang Y (2008) I-TASSER server for protein 3D structure prediction. *BMC bioinformatics* 9:40.
30. Rullo A & Nitz M (2010) Importance of the spatial display of charged residues in heparin-peptide interactions. *Biopolymers* 93(3):290-298.
31. Jayaraman G, et al. (2000) Binding of a de novo designed peptide to specific glycosaminoglycans. *FEBS letters* 482(1):154-158.
32. Inoue S, Kawano H, Ishihara T, Maeda S, & Ohno S (2005) Formation of experimental murine AA amyloid fibrils in SAP-deficient mice: high resolution ultrastructural study. *Amyloid* 12(3):157-163.
33. Wall J S, et al. (2013) A binding-site barrier affects imaging efficiency of high affinity amyloid-reactive Peptide radiotracers in vivo. *PloS one* 8(6):e66181.
34. Console S (2003) Antennapedia and HIV Transactivator of Transcription (TAT) "Protein Transduction Domains" Promote Endocytosis of High Molecular Weight Cargo upon Binding to Cell Surface Glycosaminoglycans. *Journal of Biological Chemistry* 278.
35. Fang S-l, et al. (2013) A novel cell-penetrating peptide derived from human eosinophil cationic protein. *PloS one* 8(3).
36. Payne C K, Jones S A, Chen C, & Zhuang X (2007) Internalization and trafficking of cell surface proteoglycans and proteoglycan-binding ligands. *Traffic* 8(4):389-401.
37. Lewin M, et al. (2000) Tat peptide-derivatized magnetic nanoparticles allow in vivo tracking and recovery of progenitor cells. *Nature biotechnology* 18(4):410-414.
38. Schwarze S R, Hruska K A, & Dowdy S F (2000) Protein transduction: unrestricted delivery into all cells? *Trends Cell Biol* 10(7):290-295.
39. Tiwari V, Liu J, Valyi-Nagy T, & Shukla D (2011) Anti-heparan sulfate peptides that block herpes simplex virus infection in vivo. *The Journal of biological chemistry* 286(28):25406-25415.
40. Borst E, et al. (2013) A peptide inhibitor of cytomegalovirus infection from human hemofiltrate. *Antimicrobial agents and chemotherapy* 57(10):4751-4760.
41. Wall J S, Solomon A, & Kennel S J (2011) Development and evaluation of agents for targeting visceral amyloid. *Tijdschrift voor nu[c]leaire geneeskunde* 33(4):807-814.
42. Herold B C, Gerber S I, Belval B J, Siston A M, & Shulman N (1996) Differences in the susceptibility of herpes simplex virus types 1 and 2 to modified heparin compounds suggest serotype differences in viral entry. *Journal of virology* 70(6):3461-3469.
43. Kato M, Wang H, Bernfield M, Gallagher J, & Turnbull J (1994) Cell surface syndecan-1 on distinct cell types differs in fine structure and ligand binding of its heparan sulfate chains. *The Journal of biological chemistry* 269 (29):18881-18890.
44. Lindahl U, Kusche-Gullberg M, & Kjellén L (1998) Regulated diversity of heparan sulfate. *The Journal of biological chemistry* 273(39):24979-24982.
45. Harvey D M & Levine A J (1991) p53 alteration is a common event in the spontaneous immortalization of primary BALB/c murine embryo fibroblasts. *Genes & development* 5(12B):2375-2385.
46. Miller W E, et al. (2012) US28 is a potent activator of phospholipase C during HCMV infection of clinically relevant target cells. *PloS one* 7(11):e50524.
47. O'Connor C M & Shenk T (2011) Human cytomegalovirus pUS27 G protein-coupled receptor homologue is required for efficient spread by the extracellular route but not for direct cell-to-cell spread. *Journal of virology* 85(8):3700-3707.
48. Dogra P, Martin E B, Williams A, Richardson R L, Foster J S, et. al. Novel heparan sulfate-binding peptides for blocking herpesvirus entry. *PLoS ONE.* 2015; 10(5): e0126239.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A heparin binding peptide consisting of an amino acid sequence at least 95% identical to the amino acid sequence set forth as any one of SEQ ID NOs: 3-10.

2. The heparin binding peptide of claim 1, wherein administration of the heparin binding peptide to a subject infected with a virus reduces viral infection in the subject.

3. The heparin binding peptide of claim 2, wherein administration of the heparin binding peptide to the subject infected with the virus reduces viral infection in the subject by at least 60%.

4. The heparin binding peptide of claim 2, wherein the virus is an enveloped DNA virus or enveloped RNA virus.

5. The heparin binding peptide of claim 1, wherein administration of the heparin binding peptide to a subject infected with herpesvirus reduces herpesvirus infection in the subject.

6. The heparin binding peptide of claim 1, wherein administration of the heparin binding peptide to a subject infected with cytomegalovirus reduces cytomegalovirus infection in the subject.

7. The heparin binding peptide of claim 1, wherein administration of the heparin binding peptide to a subject infected human immunodeficiency virus (HIV) infection reduces HIVs infection in the subject.

8. The heparin binding peptide of claim 1, wherein the heparin-binding peptide is a D-form peptide.

9. A heparin binding peptide comprising an amino acid sequence at least 95% identical to the amino acid sequence set forth as any one of SEQ ID NO: 7, SEQ ID NO: 9, and SEQ ID NO: 10.

10. The heparin binding peptide of claim 9, wherein administration of the heparin binding peptide to a subject infected with a virus reduces viral infection in the subject.

11. The heparin binding peptide of claim 10, wherein administration of the heparin binding peptide to the subject infected with the virus reduces viral infection in the subject by at least 60%.

12. The heparin binding peptide of claim 10, wherein the virus is an enveloped DNA virus or enveloped RNA virus.

13. The heparin binding peptide of claim 9, wherein administration of the heparin binding peptide to a subject infected with herpesvirus reduces herpesvirus infection in the subject.

14. The heparin binding peptide of claim 9, wherein administration of the heparin binding peptide to a subject infected with cytomegalovirus reduces cytomegalovirus infection in the subject.

15. The heparin binding peptide of claim 9, wherein administration of the heparin binding peptide to a subject infected human immunodeficiency virus (HIV) infection reduces HIVs infection in the subject.

16. The heparin binding peptide of claim 9, wherein the heparin-binding peptide is a D-form peptide.

* * * * *

SEQUENCE LISTING

```
<160> NUMBER OF SEQ ID NOS: 25

<210> SEQ ID NO 1
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(27)
<223> OTHER INFORMATION: Xaa for residues 1, 3-4, 6-8, 10-11, 13-15,
      17-18, 20-22, 24-25, and 27 is any amino acid, such as alanine,
      valine, serine, threonine, or glycine or X is a modified amino
      acid that is not charged.
<220> FEATURE:
<221> NAME/KEY: VARIANT
<222> LOCATION: (1)..(27)
<223> OTHER INFORMATION: Xaa for residues 2, 5, 9, 12, 16, 19, 23, and
      26 is a positively charged amino acid, such as arginine, lysine,
      or histidine.
```

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: PEPTIDE
<222> LOCATION: (1)..(26)
<223> OTHER INFORMATION: Xaa at residues 1, 4, 8, 11, 15, 18, 22, and 25
      is Arg, Lys, or His.
<220> FEATURE:
<221> NAME/KEY: PEPTIDE
<222> LOCATION: (1)..(26)
<223> OTHER INFORMATION: Xaa at residues 2, 5, 7, 10, 13, 16, 19, 21,
      and 24 is Ile, Leu, Met, Val, Gly, Phe, Trp, Tyr, Ser, Thr, Asp,
      or a modified amino acid that is not charged.
<220> FEATURE:
<221> NAME/KEY: PEPTIDE
<222> LOCATION: (1)..(26)
<223> OTHER INFORMATION: Xaa at residues 3, 6, 9, 12, 14, 17, 20, 23,
      and 26 is Ile, Leu, Met, Val, Gly, Phe, Trp, Tyr, Ser, Thr, Asp,
      or a modified amino acid that is not charged.

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 3
<211> LENGTH: 26
<212> TYPE: PRT
<213> ORGANISM: Artificial Sequence
<220> FEATURE:
<223> OTHER INFORMATION: Peptide p5 Synthetic Construct
<220> FEATURE:
<221> NAME/KEY: PEPTIDE
<222> LOCATION: (1)..(26)

<400> SEQUENCE: 3

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln
            20                  25

<210> SEQ ID NO 4
<211> LENGTH: 40
<212> TYPE: PRT
<213> ORGANISM: Artificial Sequence
<220> FEATURE:
<223> OTHER INFORMATION: Peptide P5+14 Synthetic Construct
<220> FEATURE:
<221> NAME/KEY: PEPTIDE
<222> LOCATION: (1)..(40)

<400> SEQUENCE: 4

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Gln Lys Ala Gln Lys
            20                  25                  30

```
Ala Gln Ala Lys Gln Ala Lys Gln
        35                  40

<210> SEQ ID NO 5
<211> LENGTH: 40
<212> TYPE: PRT
<213> ORGANISM: Artificial Sequence
<220> FEATURE:
<223> OTHER INFORMATION: Peptide p5R+14 Synthetic Construct
<220> FEATURE:
<221> NAME/KEY: PEPTIDE
<222> LOCATION: (1)..(40)

<400> SEQUENCE: 5

Arg Ala Gln Arg Ala Gln Ala Arg Gln Ala Arg Gln Ala Gln Arg Ala
1               5                   10                  15

Gln Arg Ala Gln Ala Arg Gln Ala Arg Gln Ala Gln Arg Ala Gln Arg
            20                  25                  30

Ala Gln Ala Arg Gln Ala Arg Gln
        35                  40

<210> SEQ ID NO 6
<211> LENGTH: 26
<212> TYPE: PRT
<213> ORGANISM: Artificial Sequence
<220> FEATURE:
<223> OTHER INFORMATION: Peptide p5R Synthetic Construct
<220> FEATURE:
<221> NAME/KEY: PEPTIDE
<222> LOCATION: (1)..(26)

<400> SEQUENCE: 6

Arg Ala Gln Arg Ala Gln Ala Arg Gln Ala Arg Gln Ala Gln Arg Ala
1               5                   10                  15

Gln Arg Ala Gln Ala Arg Gln Ala Arg Gln
            20                  25

<210> SEQ ID NO 7
<211> LENGTH: 26
<212> TYPE: PRT
<213> ORGANISM: Artificial Sequence
<220> FEATURE:
<223> OTHER INFORMATION: Peptide P10 Synthetic Construct
<220> FEATURE:
<221> NAME/KEY: PEPTIDE
<222> LOCATION: (1)..(26)

<400> SEQUENCE: 7

Lys Gly Gly Lys Gly Gly Gly Lys Gly Gly Lys Gly Gly Gly Lys Gly
1               5                   10                  15

Gly Lys Gly Gly Gly Lys Gly Gly Lys Gly
            20                  25

<210> SEQ ID NO 8
<211> LENGTH: 41
<212> TYPE: PRT
<213> ORGANISM: Artificial Sequence
<220> FEATURE:
<223> OTHER INFORMATION: Peptide p14 Synthetic Construct
<220> FEATURE:
<221> NAME/KEY: PEPTIDE
<222> LOCATION: (1)..(41)

<400> SEQUENCE: 8

Ala Lys Tyr Gln Lys Ala Gln Ala Lys Ala Gln Ala Lys Ala Gln Arg
1               5                   10                  15
```

```
Ala Gln Arg Ala Gln Ala Arg Gln Ala Arg Gln Ala Gln Ala Gln
            20                  25                  30

Arg Ala Gln Ala Arg Gln Ala Arg Gln
            35                  40

<210> SEQ ID NO 9
<211> LENGTH: 29
<212> TYPE: PRT
<213> ORGANISM: Artificial Sequence
<220> FEATURE:
<223> OTHER INFORMATION: Peptide p9 Synthetic Construct
<220> FEATURE:
<221> NAME/KEY: PEPTIDE
<222> LOCATION: (1)..(29)

<400> SEQUENCE: 9

Lys Ala Gln Ala Lys Ala Gln Ala Lys Ala Gln Ala Lys Ala Gln Ala
1               5                   10                  15

Lys Ala Gln Ala Lys Ala Gln Ala Lys Ala Gln Ala Lys
            20                  25

<210> SEQ ID NO 10
<211> LENGTH: 18
<212> TYPE: PRT
<213> ORGANISM: Artificial Sequence
<220> FEATURE:
<223> OTHER INFORMATION: Peptide p42 Synthetic Construct
<220> FEATURE:
<221> NAME/KEY: PEPTIDE
<222> LOCATION: (1)..(18)

<400> SEQUENCE: 10

Val Tyr Lys Val Lys Thr Lys Val Lys Thr Lys Val Lys Thr Lys Val
1               5                   10                  15

Lys Thr

<210> SEQ ID NO 11
<211> LENGTH: 31
<212> TYPE: PRT
<213> ORGANISM: Artificial Sequence
<220> FEATURE:
<223> OTHER INFORMATION: Peptide CGGY-p5e Synthetic Construct
<220> FEATURE:
<221> NAME/KEY: PEPTIDE
<222> LOCATION: (6)..(31)

<400> SEQUENCE: 11

Cys Gly Gly Tyr Ser Glu Ala Gln Glu Ala Gln Ala Glu Gln Ala Glu
1               5                   10                  15

Gln Ala Gln Glu Ala Gln Glu Ala Gln Ala Glu Gln Ala Glu Gln
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Peptide CGGY-p5L Synthetic Construct
<220> FEATURE:
<221> NAME/KEY: PEPTIDE
<222> LOCATION: (6)..(31)

<400> SEQUENCE: 12

Cys Gly Gly Tyr Ser Leu Ala Gln Leu Ala Gln Ala Leu Gln Ala Leu
1               5                   10                  15

Gln Ala Gln Leu Ala Gln Leu Ala Gln Ala Leu Gln Ala Leu Gln
```

20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Peptide CGGYp5G Synthetic Construct
<220> FEATURE:
<221> NAME/KEY: PEPTIDE
<222> LOCATION: (6)..(31)

<400> SEQUENCE: 13

Cys Gly Gly Tyr Ser Gly Ala Gln Gly Ala Gln Ala Gly Gln Ala Gly
1               5                   10                  15

Gln Ala Gln Gly Ala Gln Gly Ala Gln Ala Gly Gln Ala Gly Gln
            20                  25                  30

<210> SEQ ID NO 14
<211> LENGTH: 12
<212> TYPE: PRT
<213> ORGANISM: Artificial Sequence
<220> FEATURE:
<223> OTHER INFORMATION: Peptide G2 Synthetic Construct
<220> FEATURE:
<221> NAME/KEY: PEPTIDE
<222> LOCATION: (1)..(12)

<400> SEQUENCE: 14

Met Pro Arg Arg Arg Arg Ile Arg Arg Gln Lys
1               5                   10

<210> SEQ ID NO 15
<211> LENGTH: 26
<212> TYPE: PRT
<213> ORGANISM: Artificial Sequence
<220> FEATURE:
<223> OTHER INFORMATION: Heparin Binding Peptide Synthetic Construct
<220> FEATURE:
<221> NAME/KEY: PEPTIDE
<222> LOCATION: (1)..(26)

<400> SEQUENCE: 15

Arg Ala Gln Arg Ala Gln Ala Arg Gln Ala Arg Gln Ala Gln Arg Ala
1               5                   10                  15

Gln Arg Ala Gln Ala Arg Gln Ala Arg Gln
            20                  25

<210> SEQ ID NO 16
<211> LENGTH: 26
<212> TYPE: PRT
<213> ORGANISM: Artificial Sequence
<220> FEATURE:
<223> OTHER INFORMATION: Heparin Binding Peptide Synthetic Construct
<220> FEATURE:
<221> NAME/KEY: PEPTIDE
<222> LOCATION: (1)..(26)

<400> SEQUENCE: 16

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln
            20                  25

<210> SEQ ID NO 17
<211> LENGTH: 7
<212> TYPE: PRT

```
<213> ORGANISM: Artificial Sequence
<220> FEATURE:
<223> OTHER INFORMATION: Peptide Repeat Sequence Synthetic Construct
<220> FEATURE:
<221> NAME/KEY: REPEAT
<222> LOCATION: (1)..(7)

<400> SEQUENCE: 17

Lys Ala Gln Lys Ala Gln Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Peptide Repeat Sequence Synthetic Construct
<220> FEATURE:
<221> NAME/KEY: REPEAT
<222> LOCATION: (1)..(7)

<400> SEQUENCE: 18

Lys Gln Ala Lys Gln Ala Gln
1               5

<210> SEQ ID NO 19
<211> LENGTH: 5
<212> TYPE: PRT
<213> ORGANISM: Artificial Sequence
<220> FEATURE:
<223> OTHER INFORMATION: Functional Leader Sequence Synthetic Construct

<400> SEQUENCE: 19

Gly Gly Gly Tyr Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Heptad amino acid repeat Synthetic Construct
<220> FEATURE:
<221> NAME/KEY: REPEAT
<222> LOCATION: (1)..(7)

<400> SEQUENCE: 20

Lys Ala Gln Lys Ala Gln Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Anti-viral Peptide Synthetic Construct
<220> FEATURE:
<221> NAME/KEY: PEPTIDE
<222> LOCATION: (1)..(5)

<400> SEQUENCE: 21

Cys Tyr Val Ile Pro
1               5

<210> SEQ ID NO 22
<211> LENGTH: 31
<212> TYPE: PRT
<213> ORGANISM: Artificial Sequence
<220> FEATURE:
```

```
<223> OTHER INFORMATION: Peptide CGGY-p5 Synthetic Construct
<220> FEATURE:
<221> NAME/KEY: PEPTIDE
<222> LOCATION: (6)..(31)

<400> SEQUENCE: 22

Cys Gly Gly Tyr Ser Lys Ala Gln Lys Ala Gln Ala Lys Gln Ala Lys
1               5                   10                  15
Gln Ala Gln Lys Ala Gln Lys Ala Gln Ala Lys Gln Ala Lys Gln
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: CGGY-p5 peptide Synthetic Construct
<220> FEATURE:
<221> NAME/KEY: PEPTIDE
<222> LOCATION: (6)..(31)

<400> SEQUENCE: 23

Gly Gly Gly Tyr Ser Lys Ala Gln Lys Ala Gln Ala Lys Gln Ala Lys
1               5                   10                  15
Gln Ala Gln Lys Ala Gln Lys Ala Gln Ala Lys Gln Ala Lys Gln
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: CGGY-p5R Peptide Synthetic Construct
<220> FEATURE:
<221> NAME/KEY: PEPTIDE
<222> LOCATION: (6)..(31)

<400> SEQUENCE: 24

Gly Gly Gly Tyr Ser Arg Ala Gln Arg Ala Gln Ala Arg Gln Ala Arg
1               5                   10                  15
Gln Ala Gln Arg Ala Gln Arg Ala Gln Ala Arg Gln Ala Arg Gln
            20                  25                  30

<210> SEQ ID NO 25
<211> LENGTH: 45
<212> TYPE: PRT
<213> ORGANISM: Artificial Sequence
<220> FEATURE:
<223> OTHER INFORMATION: CGGY-p5+14 Peptide Synthetic Construct
<220> FEATURE:
<221> NAME/KEY: PEPTIDE
<222> LOCATION: (6)..(45)

<400> SEQUENCE: 25

Gly Gly Gly Tyr Ser Lys Ala Gln Lys Ala Gln Ala Lys Gln Ala Lys
1               5                   10                  15
Gln Ala Gln Lys Ala Gln Lys Ala Gln Ala Lys Gln Ala Lys Gln Ala
            20                  25                  30
Gln Lys Ala Gln Lys Ala Gln Ala Lys Gln Ala Lys Gln
        35                  40                  45
```